US006881749B2

(12) United States Patent
Chen et al.

(10) Patent No.: US 6,881,749 B2
(45) Date of Patent: *Apr. 19, 2005

(54) PYRANOINDAZOLES AND THEIR USE FOR THE TREATMENT OF GLAUCOMA

(75) Inventors: Hwang-Hsing Chen, Fort Worth, TX (US); Jesse A. May, Fort Worth, TX (US); Bryon S. Severns, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/722,042

(22) Filed: Nov. 24, 2003

(65) Prior Publication Data

US 2004/0106609 A1 Jun. 3, 2004

Related U.S. Application Data

(63) Continuation of application No. PCT/US02/16861, filed on May 30, 2002.
(60) Provisional application No. 60/295,429, filed on Jun. 1, 2001.

(51) Int. Cl.$^7$ ..................... A61K 31/416; C07D 491/02
(52) U.S. Cl. .................................... 514/403; 548/359.5
(58) Field of Search ........................ 548/359.5; 514/403

(56) References Cited

U.S. PATENT DOCUMENTS

| | | | | |
|---|---|---|---|---|
| 4,690,931 A | | 9/1987 | Wick et al. ................ | 514/317 |
| 5,151,444 A | | 9/1992 | Ueno et al. ................ | 514/530 |
| 5,296,504 A | | 3/1994 | Stjernschantz et al. ..... | 514/530 |
| 5,352,708 A | | 10/1994 | Woodward et al. ......... | 514/729 |
| 5,422,368 A | | 6/1995 | Stjernschantz et al. ..... | 514/530 |
| 5,494,928 A | | 2/1996 | Bös ............................ | 514/415 |
| 5,561,150 A | | 10/1996 | Wichmann .................. | 514/406 |
| 5,571,833 A | | 11/1996 | Kruse et al. ................ | 514/414 |
| 5,578,612 A | | 11/1996 | Macor et al. ............... | 514/323 |
| 5,646,173 A | | 7/1997 | Bös et al. ................... | 514/411 |
| 5,874,477 A | | 2/1999 | McConnell et al. ........ | 514/657 |
| 5,889,052 A | | 3/1999 | Klimko et al. ............. | 514/530 |
| 5,902,815 A | | 5/1999 | Olney et al. ............... | 514/284 |
| 6,245,796 B1 | * | 6/2001 | Maeno et al. ............... | 514/403 |
| 6,548,493 B1 | | 4/2003 | Robichaud et al. .... | 514/212.05 |
| 6,552,017 B1 | | 4/2003 | Robichaud et al. ......... | 514/219 |
| 6,696,476 B1 | * | 2/2004 | Chen et al. ................. | 514/403 |
| 6,713,471 B1 | | 3/2004 | Robichaud et al. ...... | 514/211.1 |
| 2004/0034015 A1 | | 2/2004 | Robichaud et al. ......... | 514/219 |

FOREIGN PATENT DOCUMENTS

| | | | |
|---|---|---|---|
| EP | 0771563 A2 | 5/1997 | |
| EP | 0990650 A1 | 4/2000 | |
| WO | WO 92/20338 | 11/1992 | |
| WO | WO 94/13275 | 6/1994 | |
| WO | WO 97/33579 | 9/1997 | |
| WO | WO 98/18458 | 5/1998 | |
| WO | WO 98/30548 | 7/1998 | |
| WO | WO 98/31354 | 7/1998 | |
| WO | WO 98/56768 | 12/1998 | |
| WO | WO 00/12475 | 3/2000 | |
| WO | WO 00/12510 | 3/2000 | |
| WO | WO 00/16761 | 3/2000 | |
| WO | WO 00/35922 | 6/2000 | |
| WO | WO 00/44753 | 8/2000 | |
| WO | WO 01/70701 A1 | 9/2001 | |
| WO | WO 01/83487 | 11/2001 | ................ 491/48 |

OTHER PUBLICATIONS

Osborne, et al. "Do Beta–Adrenoceptors and Serotonin 5–HT$_{1A}$ Receptors Have Similar Functions in the Control of Intraocular Pressure in the Rabbit?" *Ophthalmologica*, vol. 210, pp. 308–314 (1996).
Wang, et al., "Effect of 5–methylurapidil, an $\alpha_{1a}$–adrenergic antagonist and 5–hydroxytryptamine$_{1a}$ agonist, on aqueous humor dynamics in monkeys and rabbits" *Current Eye Research*, vol. 16(8) pp. 769–775 (1997).
IOVS, *Aqueous Humor Dynamics I*, vol. 39(4), S488, 2236–B93, (1998).
Fiorella, "Role of 5–HT$_{2A}$ and 5–HT$_{2C}$ receptors in the stimulus effects of hallucinogenic drugs II: reassessment of LSD false positives," *Psychopharmacology*, vol. 121:357–363, 1995.
Frigerio, et al., "Oxidation of Alcohols with o–Iodoxybenzoic Acid (IBX) in DMSO: A New Insight into an Old Hypervalent Iodine Reagent" *J. Org. Chem.* 60, pp 7272–7276 (1995).
Portal et al. "The Synthesis of Benzo (b) Thieno and Benzo (b) Furo Indazole Derivatives. The Report of Three Novel Heterocyclic Systems." *Anales Assoc. Quim. Argentina* 59, 69–76 (1971).
Clark et al., "Heterocyclic Studies. Part 42. Pyrimido[5,4–d][1,2,3]triazines and some Related Tricyclic Compounds" *J. Chem. Soc., Perkins* vol. 1, pp. 1475–1481 (1984).
Lown et al., "Formation of Novel 1,2–Oxathietanes from 2–Chloroethyl Sulfoxide Precursors and Their Reactions in Solution, Including Formal [σ2s + σ2a] Cycloreversions and Rearrangements" *J. Amer. Chem. Soc.*, vol. 108, No. 13, pp. 3811–3818 (1986).
Benson, Jr. et al., "N–Alkyl–5, 5–dimethyl–2–oxomorpholin–3–YI Radicals. Characterization and Reaction with Molecular Oxygen." *J. Amer. Chem. Soc.* vol. 113, pp. 8879–8886 (1991).
Wentland et al., "Synthesis and Bacterial DNA Gyrase Inhibitory Properties of a Spirocyclopropylquinolone Derivative" *J. Med. Chem.*, vol. 31, pp. 1694–1697 (1988).

(Continued)

*Primary Examiner*—Fiona T. Powers
(74) *Attorney, Agent, or Firm*—Kilyk & Bowersox, P.L.L.C.

(57) ABSTRACT

Pyranoindazoles are disclosed. Also disclosed are methods for the lowering and controlling of normal or elevated intraocular pressure as well as a method for the treatment of glaucoma using compositions containing one or more of the compounds of the present invention.

25 Claims, No Drawings

OTHER PUBLICATIONS

Johnson, "Reaction of Aliphatic Amines with Formaldehyde and Nitroparaffins. II. Secondary Amines," *J. Amer. Chem. Soc.,* vol. 68, pp. 12–14 (1946).

Sequeria et al., "Synthesis of Fused Indazole Derivatives" *Indian J. Chem.* 26B, pp. 436–439 (1987).

Grandolini et al., "92/New Heterocyclic Ring Systems from α–Hydroxymethyleneketones. VII. Furoindazoles and Furobenzisoxazoles," *Gazz. Chim Ital.* vol. 106, pp. 1083–1094 (1976).

Plug et al., "Synthesis of Novel Annulated Ellipticines via Claisen Rearrangement Reactions," *Tetrahedron Lett.* vol. 33, pp. 2179–2182 (1992).

Macor et al., "The Synthesis of Conformationally/Rotationally Restricted Analogs of the Neurotransmitter Serotonin," *Tetrahedron Lett.* vol. 35, pp. 45–48 (1994).

Macor et al., "Studies towards understanding the mechanism of the unusual rearrangmetn of certain 5–proparglyoxyindoles," *Tetrahedron Lett.* vol. 41, pp. 3541–3545 (2000).

Johnson et al., Binding to the Serotonin 5–HT2 Receptor by the Enantiomers of $125_{I-DOI}$, *Neuropharmacology,* vol. 26, pp. 1803–1806 (1987).

Bowen et al., "Nonlinear regression using spreadsheets," *Trends Pharmacol. Sci.,* vol. 16, pp. 413–417 (1995).

Gorvin, "Aromatic nitro–group displacement reactions." *J. Chem. Res., Synop.* (4), pp. 88–89, (1991) (Abstract).

International Search Report for PCT/US02/16861 dated Dec. 11, 2002.

* cited by examiner

PYRANOINDAZOLES AND THEIR USE FOR THE TREATMENT OF GLAUCOMA

This application is a continuation of International Patent Application No. PCT/US02/16861 filed May 30, 2002, which in turn claims the benefit of U.S. Provisional Patent Application No. 60/295,429 filed Jun. 1, 2001, and is incorporated in its entirety by reference herein.

BACKGROUND OF THE INVENTION

The present invention relates to various pyranoindazoles. These novel compounds are useful for lowering and controlling normal or elevated intraocular pressure (IOP) and for treating glaucoma.

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated but no apparent loss of visual function has occurred; such patients are considered to be at high risk for the eventual development of the visual loss associated with glaucoma. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility. Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

Serotonergic 5-$HT_{1A}$ agonists have been reported as being neuroprotective in animal models and many of these agents have been evaluated for the treatment of acute stroke among other indications. This class of compounds has been mentioned for the treatment of glaucoma (lowering and controlling IOP), see e.g., WO 98/18458 (DeSantis, et al.) and EP 0771563A2 (Mano, et al.). Osborne, et al. (Ophthalmologica, Vol. 210:308–314, 1996) teach that 8-hydroxydipropylaminotetralin (8-OH-DPAT) (a 5-$HT_{1A}$ agonist) reduces IOP in rabbits. Wang, et al. (Current Eye Research, Vol. 16(8):769–775, August 1997, and IVOS, Vol. 39(4), S488, March, 1998) indicate that 5-methylurapidil, an $\alpha_{1A}$ antagonist and 5-$HT_{1A}$ agonist lowers IOP in the monkey, but due to its $\alpha_{1A}$ receptor activity. Also, 5-$HT_{1A}$ antagonists are disclosed as being useful for the treatment of glaucoma (elevated IOP) (e.g., WO 92/0338, McLees). Furthermore, DeSai, et al. (WO 97/35579) and Macor, et al. (U.S. Pat. No. 5,578,612) relate to the use of 5-$HT_1$ and 5-$HT_{1-like}$ agonists for the treatment of glaucoma (elevated IOP). These anti-migraine compounds, e.g., sumatriptan and naratriptan and related compounds, are 5-$HT_{1B,D,E,F}$ agonists.

It has been found that serotonergic compounds which possess agonist activity at 5-$HT_2$ receptors effectively lower and control normal and elevated IOP and are useful for treating glaucoma, see commonly owned co-pending application, PCT/US99/19888, incorporated in its entirety by reference herein. Compounds that act as agonists at 5-$HT_2$ receptors are well known and have shown a variety of utilities, primarily for disorders or conditions associated with the central nervous system (CNS). U.S. Pat. No. 5,494,928 relates to certain 2-(indol-1-yl)-ethylamine derivatives that are 5-$HT_{2C}$ agonists for the treatment of obsessive compulsive disorder and other CNS derived personality disorders. U.S. Pat. No. 5,571,833 relates to tryptamine derivatives that are 5-$HT_2$ agonists for the treatment of portal hypertension and migraine. U.S. Pat. No. 5,874,477 relates to a method for treating malaria using 5-$HT_{2A/2C}$ agonists. U.S. Pat. No. 5,902,815 relates to the use of 5-$HT_{2A}$ agonists to prevent adverse effects of NMDA receptor hypo-function. WO 98/31354 relates to 5-$HT_{2B}$ agonists for the treatment of depression and other CNS conditions. WO 00/12475 relates to indoline derivatives and WO 00/12510 and WO 00/44753 relate to certain indole derivatives as 5-$HT_{2B}$ and 5-$HT_{2C}$ receptor agonists for the treatment of a variety of disorders of the central nervous system, but especially for the treatment of obesity. WO 00/35922 relates to certain pyrazino[1,2-a]quinoxaline derivatives as 5-$HT_{2C}$ agonists for the treatment of obsessive compulsive disorder, depression, eating disorders, and other disorders involving the CNS. WO 00/77002 and WO 00/77010 relate to certain substituted tetracyclic pyrido[4,3-b]indoles as 5-$HT_{2C}$ agonists with utility for the treatment of central nervous system disorders including obesity, anxiety, depression, sleep disorders, cephalic pain, and social phobias among others. Agonist response at the 5-$HT_{2A}$ receptor is reported to be the primary activity responsible for hallucinogenic activity, with some lesser involvement of the 5-$HT_{2C}$ receptor possible [Psychopharmacology, Vol. 121:357, 1995].

Few furan or pyran containing fused indazoles have been reported. The chemical synthesis of 7-methyl- and 1,7-dimethyl-1H-furo[2,3-g]indazole [Gazz. Chim Ital. 106, 1083 (1976)] as well as that of 3-methyl- and 1-(4-aminophenyl)-3-methyl-1H-benzo[b]furo[2,3-g]indazole [An. Asoc. Quim. Argent. 59, 69 (1971)] has been reported without discussion of their utility. European Patent Application EP 990,650 (Intnl. Publication Number WO 98/56768) relates to substituted 2-(furo[2,3-g]indazol-1-yl)-ethylamines, such as (S)-2-(furo[2,3-g]indazol-1-yl)-1-methylethylamine, which are reported to have high selectivity and affinity for 5-$HT_{2C}$ receptors and are potentially useful for treating a variety of central nervous system disorders. The chemical synthesis of 9-methyl-1H-pyrano[2,3-g]indazol-7-one and the corresponding non-methylated compound was reported [Indian J. Chem. 26B, 436 (1987)] with no mention of utility.

U.S. Pat. Nos. 5,561,150 and 5,646,173 relate to certain tricyclic pyrazole derivative compounds which are identified as being 5-$HT_{2C}$ agonists for the treatment of CNS diseases and are primarily directed to lipophilic analogs that have a high probability of entering the brain. Similarly, WO 98/56768 relates to tricyclic 5-$HT_{2C}$ agonists for the treatment of CNS diseases. All the patents and publications mentioned above and throughout are incorporated in their entirety by reference herein.

5-Hyroxytryptamine (serotonin) does not cross the blood-brain barrier and enter the brain. However, in order to increase brain serotonin levels the administration of 5-hydroxy-tryptophan can be employed. The transport of 5-hydroxy-tryptophan into the brain readily occurs, and once in the brain 5-hydroxy-tryptophan is rapidly decarboxylated to provide serotonin.

Accordingly, there is a need to provide new compounds which avoid the disadvantages described above and which provide increased chemical stability and a desired length of therapeutic activity, for instance, in decreasing intraocular pressure and treating glaucoma.

SUMMARY OF THE PRESENT INVENTION

A feature of the present invention is to provide novel compounds which are 5-HT$_2$ agonists.

Another feature of the present invention is to provide compounds which have increased chemical stability and which are useful in lowering and controlling normal or elevated intraocular pressure and/or treating glaucoma.

Another feature of the present invention is to provide compounds which provide a desired level of therapeutic activity in lowering and controlling normal or elevated intraocular pressure and/or treating glaucoma.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a compound having the Formula I:

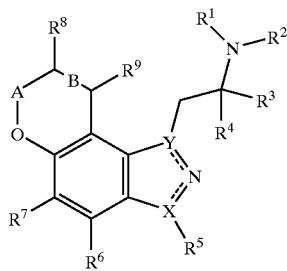

or pharmaceutically acceptable salts or solvates or prodrug forms of the compounds of Formula I. In the formula, $R^1$ and $R^2$ are independently chosen from hydrogen or an alkyl group, such as $C_{1-4}$ alkyl;
$R^3$ and $R^4$ are independently chosen from hydrogen or an alkyl group, such as $C_{1-4}$ alkyl or;
$R^3$ and $R^4$ and the carbon atom to which they are attached can form a cycloalkyl ring, or furthermore,
$R^2$ and $R^3$ together can be $(CH_2)_m$ to form a saturated heterocycle;
$R^5$ is chosen from hydrogen, halogen, an alkyl group, such as $C_{1-6}$ alkyl or $C_{1-4}$ alkyl substituted by halogen;
$R^6$ and $R^7$ are independently chosen from hydrogen, halogen, cyano, an alkylthio such as $C_{1-4}$ alkylthio, an alkyl such as $C_{1-4}$ alkyl, or a substituted alkyl such as $C_{1-4}$ alkyl substituted by halogen;
$R^8$ and $R^9$ are independently chosen from hydrogen, hydroxyl, an alkyl such as $C_{1-6}$ alkyl, an alkoxy such as $C_{1-6}$ alkoxy, =O, $NR^{10}R^{11}$, $OC(=O)NR^1R^2$, $OC(=O)C_{1-4}$alkyl, an alkylthiol such as $C_{1-6}$ alkylthiol, a substituted alkyl such as $C_{1-6}$ alkyl substituted with halogen, hydroxyl, or $NR^{10}R^{11}$;
$R^{10}$ and $R^{11}$ are independently chosen from hydrogen, an alkyl group such as $C_{1-4}$ alkyl, $C(=O)C_{1-4}$ alkyl, $C(=O)$ $OC_{1-4}$ alkyl, $C(=O)NR^1R^2$, or a substituted alkyl such as $C_{1-6}$ alkyl substituted with halogen, hydroxyl, $NR^1R^2$ or $R^{10}$ and $R^{11}$ together can complete a saturated 5 or 6-membered heterocyclic ring, which can include an additional heteroatom selected from N, O, or S when a 6-membered ring;
A is $(CH_2)_n$, C=O, or $CHC_{1-4}$alkyl;
B is either a single or a double bond, wherein when B is a double bond, $R^8$ and $R^9$ are selected from hydrogen, or a substituted or unsubstituted alkyl group;
m=2–4;
n=0–2;
X and Y are either N or C, wherein X and Y are different from each other; and the dashed bonds denote a suitably appointed single and double bond.

The present invention further relates to pharmaceutical compositions containing at least one compound of Formula I.

The present invention further relates to methods to lower and/or control normal or elevated intraocular pressure by administering an effective amount of a composition containing a compound having Formula I as described above.

The present invention also relates to a method for treating glaucoma which involves administering an effective amount of a composition containing a compound having Formula I as described above.

It is to be understood that both the foregoing general description and the following detailed description are exemplary and explanatory only and are intended to provide a further explanation of the present invention, as claimed.

DETAILED DESCRIPTION OF THE PRESENT INVENTION

The present invention relates to a variety of compounds which are useful according to the present invention. These compounds are generally represented by the following Formula I.

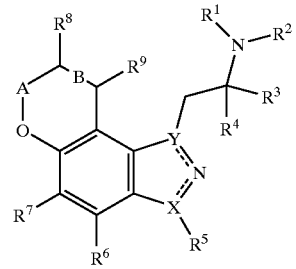

In the formula, $R^1$ and $R^2$ are independently chosen from hydrogen or an alkyl group, such as $C_{1-4}$ alkyl;
$R^3$ and $R^4$ are independently chosen from hydrogen or an alkyl group, such as $C_{1-4}$ alkyl or;
$R^3$ and $R^4$ and the carbon atom to which they are attached can form a cycloalkyl ring (e.g., cyclopropyl ring), or furthermore,
$R^2$ and $R^3$ together can be $(CH_2)_m$ to form a saturated heterocycle;
$R^5$ is chosen from hydrogen, halogen, a substituted or unsubstituted alkyl group, such as $C_{1-6}$ alkyl or $C_{1-4}$ alkyl substituted by halogen;
$R^6$ and $R^7$ are independently chosen from hydrogen, halogen, cyano, an alkylthio such as $C_{1-4}$ alkylthio, an alkyl such as $C_{1-4}$ alkyl, or a substituted alkyl such as $C_{1-4}$ alkyl substituted by halogen;
$R^8$ and $R^9$ are independently chosen from hydrogen, hydroxyl, an alkyl such as $C_{1-6}$ alkyl, an alkoxy such as $C_{1-6}$ alkoxy, =O, $NR^{10}R^{11}$, $OC(=O)NR^1R^2$, $OC(=O)$ $C_{1-4}$alkyl, an alkylthiol such as $C_{1-6}$ alkylthiol, a substituted alkyl such as $C_{1-6}$ alkyl substituted with halogen, hydroxyl, or $NR^{10}R^{11}$;

$R^{10}$ and $R^{11}$ are independently chosen from hydrogen, an alkyl group such as $C_{1-4}$ alkyl, $C(=O)C_{1-4}$ alkyl, $C(=O)OC_{1-4}$ alkyl, $C(=O)NR^1R^2$, or a substituted alkyl group such as $C_{1-6}$ alkyl substituted with halogen, hydroxyl, or $NR^1R^2$, or $R^{10}$ and $R^{11}$ together can complete a saturated 5 or 6-membered heterocyclic ring, which can include an additional heteroatom selected from N, O, or S when a 6-membered ring;

A is $(CH_2)_n$, $C=O$, or $CHC_{1-4}$alkyl;

B is either a single or a double bond, wherein when B is a double bond, $R^8$ and $R^9$ are selected from hydrogen, an alkyl group, such as $C_{1-4}$alkyl, or a substituted alkyl group, such as a $C_{1-4}$alkyl substituted by halogen, hydroxyl, or $NR^{10}R^{11}$;

m=2–4;

n=0–2;

X and Y are either N or C, wherein X and Y are different from each other; and the dashed bonds denote a suitably appointed single and double bond.

Pharmaceutically acceptable salts and solvates, and prodrug forms of the compounds of Formula I are also part of the present invention.

Preferred Compounds are:

Wherein $R^1$ and $R^2$ are independently chosen from hydrogen or $C_{1-4}$alkyl;

$R^3$ and $R^4$ are independently chosen from hydrogen, $C_{1-4}$alkyl, or $R^2$ and $R^3$ together can be $(CH_2)_m$ to form a saturated heterocycle;

$R^5$ is chosen from hydrogen, halogen, or $C_{1-6}$alkyl;

$R^6$ and $R^7$ are independently chosen from hydrogen, halogen, cyano, $C_{1-4}$alkylthio, $C_{1-4}$alkyl, or $C_{1-4}$alkyl substituted by halogen;

$R^8$ and $R^9$ are chosen from hydrogen, hydroxyl, $C_{1-6}$alkyl, $C_{1-6}$alkoxy, $NR^{10}R^{11}$, or $C_{1-6}$alkyl substituted with halogen, hydroxyl, or $NR^{10}R^{11}$;

$R^{10}$ and $R^{11}$ are independently chosen from hydrogen, $C_{1-4}$alkyl, $C(=O)C_{1-4}$alkyl, $C(=O)OC_{1-4}$ alkyl, $C(=O)NR^1R^2$, or $R^{10}$ and $R^{11}$ together can complete a saturated 6-membered heterocyclic ring, which can include an additional heteroatom selected from N, O, or S;

A is $(CH_2)_n$ or $CHC_{1-4}$alkyl;

B is either a single or double bond, wherein when B is a double bond, $R^8$ and $R^9$ are selected from hydrogen, $C_{1-4}$alkyl, or $C_{1-4}$alkyl substituted by halogen, hydroxy, or $NR^{10}R^{11}$;

m=3–4;

n=1–2;

X and Y are either N or C, wherein X and Y are different; and the dashed bonds denote a suitably appointed single and double bond;

Most Preferred Compounds are:

Wherein $R^1$ and $R^2$ are independently chosen from hydrogen or $C_{1-4}$alkyl;

$R^3$ is $C_{1-2}$alkyl, or $R^2$ and $R^3$ together can be $(CH_2)_3$ to form pyrrolidine;

$R^4$ is hydrogen;

$R^5$ is chosen from hydrogen or $C_{1-6}$alkyl;

$R^6$ and $R^7$ are independently chosen from hydrogen, halogen, or $C_{1-4}$alkyl;

$R^8$ and $R^9$ are independently chosen from hydrogen, hydroxyl, $C_{1-6}$alkoxy, $NR^{10}R^{11}$, or $C_{1-6}$alkyl substituted with hydroxyl or $NR^{10}R^{11}$;

$R^{10}$ and $R^{11}$ are independently chosen from hydrogen, $C_{1-4}$alkyl, $C(=O)C_{1-4}$alkyl, or $R^{10}$ and $R^{11}$ together can complete a saturated 6-membered heterocyclic ring, which can include an additional heteroatom selected from N, O, or S;

A is $(CH_2)_n$;

B is a single bond;

n=1;

X is C and Y is N; and the dashed bonds denote a suitably appointed single and double bond.

Representative Examples of Preferred Compounds of Formula I are:

1-(2-Aminopropyl)-1,7,8,9-tetrahydro-pyrano[2,3-g]indazol-8-ol;

1-((S)-2-Aminopropyl)-1,7,8,9-tetrahydro-pyrano[2,3-g]indazol-8-ol;

(R)-1-((S)-2-Aminopropyl)-1,7,8,9-tetrahydro-pyrano[2,3-g]indazol-8-ol;

(S)-1-((S)-2-Aminopropyl)-1,7,8,9-tetrahydro-pyrano[2,3-g]indazol-8-ol;

1-((S)-2-Aminopropyl)-3-methyl-1,7,8,9-tetrahydro-pyrano[2,3-g]indazol-8-ol;

1-(S)-1-Pyrrolidin-2-ylmethyl-1,7,8,9-tetrahydro-pyrano[2,3-g]indazol-8-ol;

1-((S)-2-Aminopropyl)-5-fluoro-1,7,8,9-tetrahydro-pyrano[2,3-g]indazol-8-ol;

(R)-1-((S)-2-Aminopropyl)-1,7,8,9-tetrahydro-pyrano[2,3-g]indazol-8-ylamine;

[1-((S)-2-Aminopropyl)-1,7,8,9-tetrahydro-pyrano[2,3-g]indazol-8-yl]-dimethylamine;

[1-((S)-2-Aminopropyl)-1,7,8,9-tetrahydro-pyrano[2,3-g]indazol-8-yl]-methanol;

1-((S)-2-Aminopropyl)-1,7,8,9-tetrahydro-pyrano[2,3-g]indazole-8,9-diol;

1-((S)-2-Aminopropyl)-9-methoxy-1,7,8,9-tetrahydro-pyrano[2,3-g]indazol-8-ol;

1-(2-Aminopropyl)-3,7,8,9-tetrahydro-pyrano[3,2-e]indazol-8-ol;

1-(Pyrrolidin-2-ylmethyl)-3,7,8,9-tetrahydro-pyrano[3,2-e]indazol-8-ol;

1-((S)-2-Aminopropyl)-3,7,8,9-tetrahydro-pyrano[3,2-e]indazol-8-ol;

1-((S)-2-Aminopropyl)-3-methyl-3,7,8,9-tetrahydro-pyrano[3,2-e]indazol-8-ol; or combinations thereof.

Certain compounds of Formula I can contain one or more chiral centers. The present invention contemplates all enantiomers, diastereomers, and mixtures thereof.

In the above definitions, the total number of carbon atoms in a substituent group is indicated by the $C_{i-j}$ prefix where the numbers i and j define the number of carbon atoms. This definition includes straight chain, branched chain, and cyclic alkyl or (cyclic alyky) alkyl groups. A substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

Synthesis

The compounds of Formula I can be prepared by using one of several synthetic procedures. For example, 1-(2-aminopropyl)-1,7,8,9-tetrahydro-pyrano[2,3-g]indazol-8-ols can be prepared from an appropriately protected 1-(6-hydroxyindazol-1-yl)-propan-2-ol 1 as outlined in Scheme 1. Pg denotes a suitable protective group to assure that a particular atom is not modified during the indicated chemical reaction.

Scheme 1

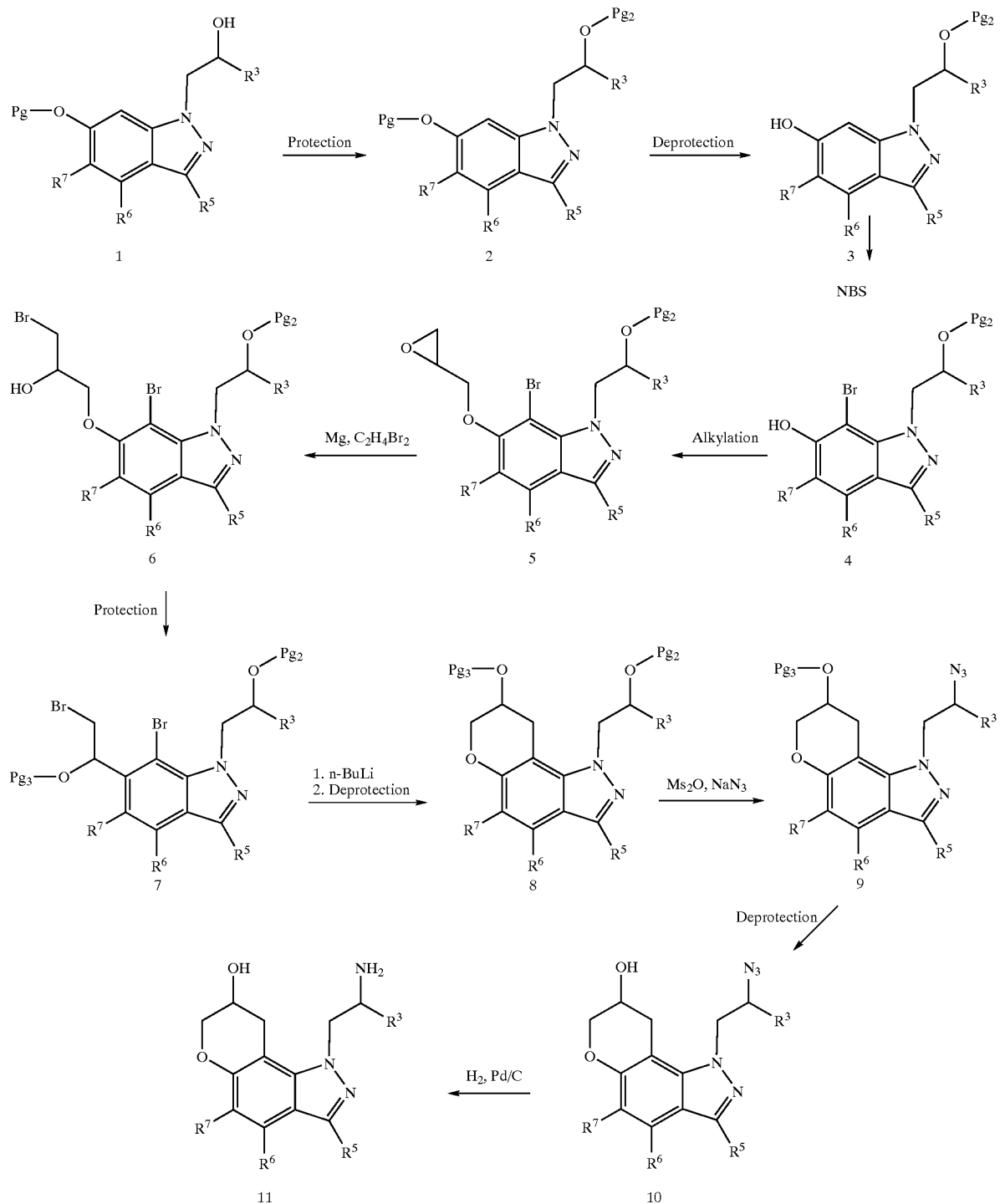

Other compounds of Formula I can be prepared from 12 through selected functional group transformations well known in the art For example, initial protection of the primary amine group followed by activation of the hydroxyl group by formation of a sulfonate ester, e.g. methanesulfonyl, and subsequent reaction with a desired nucleophile such as alkylamines, dialkylamines, aryl or alkylthiols, and the like, will provide compounds 14 of Formula I. Furthermore, direct oxidation of 13 with a suitable oxidizing agent, for example, a hypervalent iodine reagent, such as o-iodoxybenzoic acid [*J. Org. Chem.* 60, 7272 (1995)], provides the ketone 16, which can be functionalized to provide yet other compounds of Formula I, such as 17, via reductive alkylation, and 15, via Grignard addition.

Scheme 2

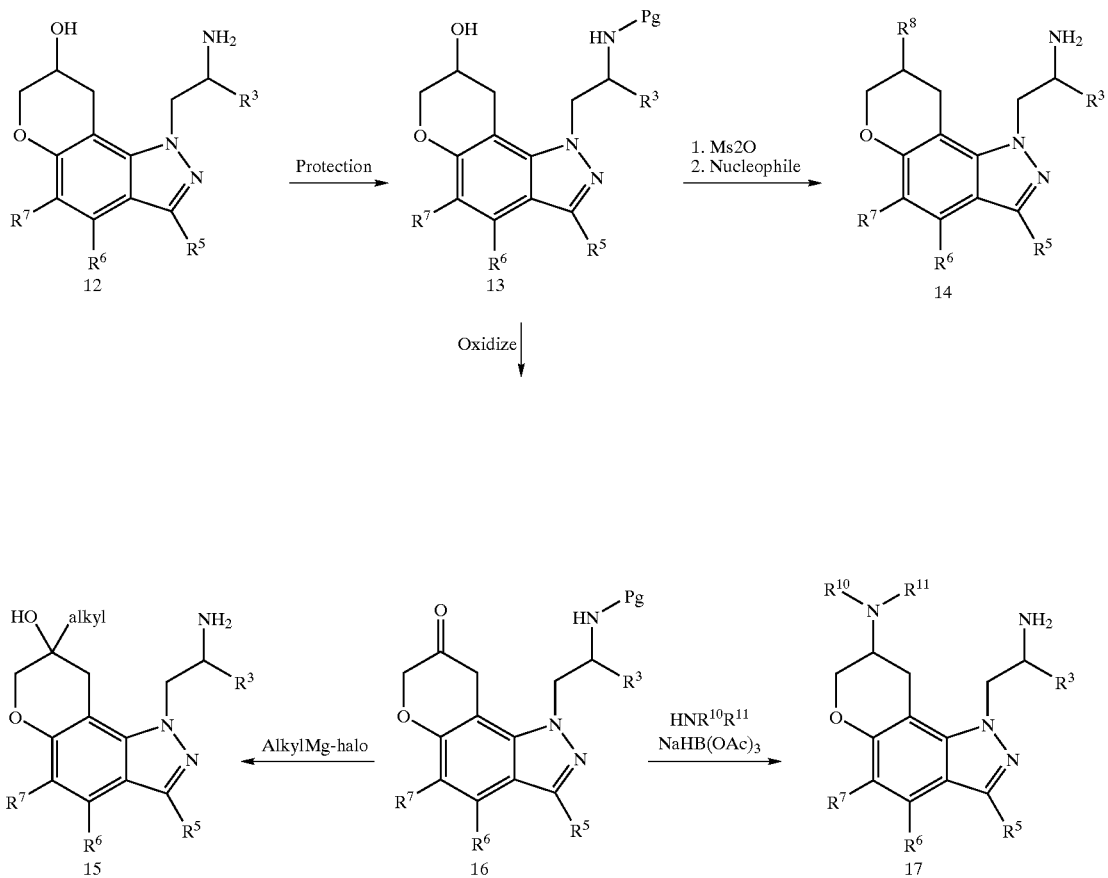

Alternately, compounds of Formula I can be prepared from appropriately substituted 5-propargyloxy-indazoles (19) via initial Claisen rearrangement reactions [*Tetrahedron Lett.* 33, 2179 (1992), ibid. 35, 45 (1994), ibid. 41, 3541 (2000)] to give the intermediate substituted pyrano[2,3-g] indazoles 20 (Scheme 3). Further synthetic manipulation of 20, for example, as outlined in Schemes 3–5, using well-known functional group transformations provides yet other desirable compounds of Formula I.

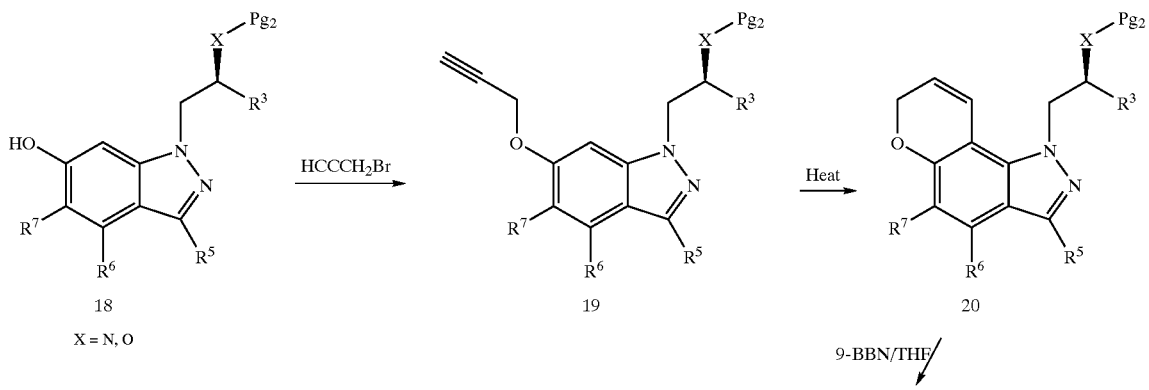

-continued
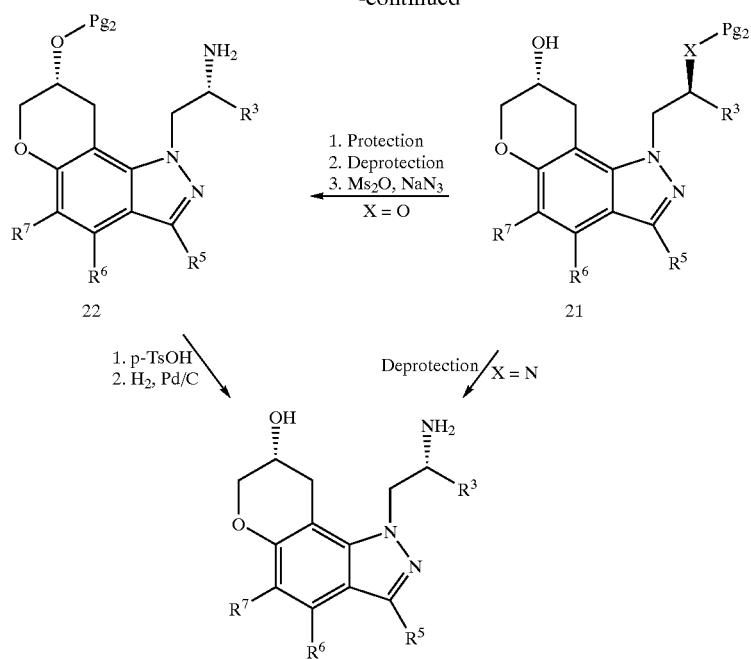
Scheme 4
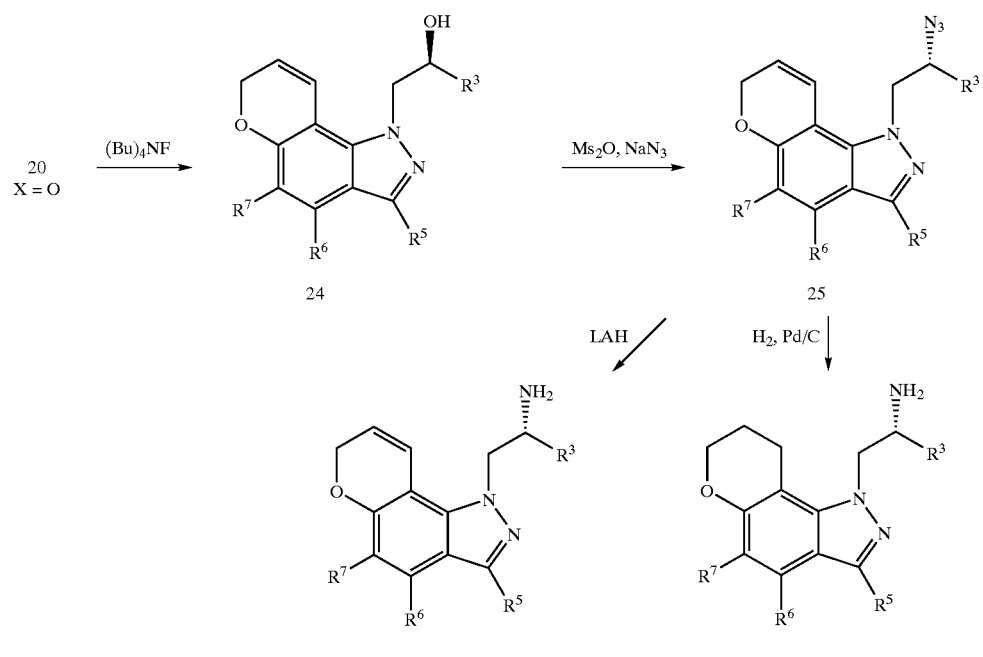

Scheme 5

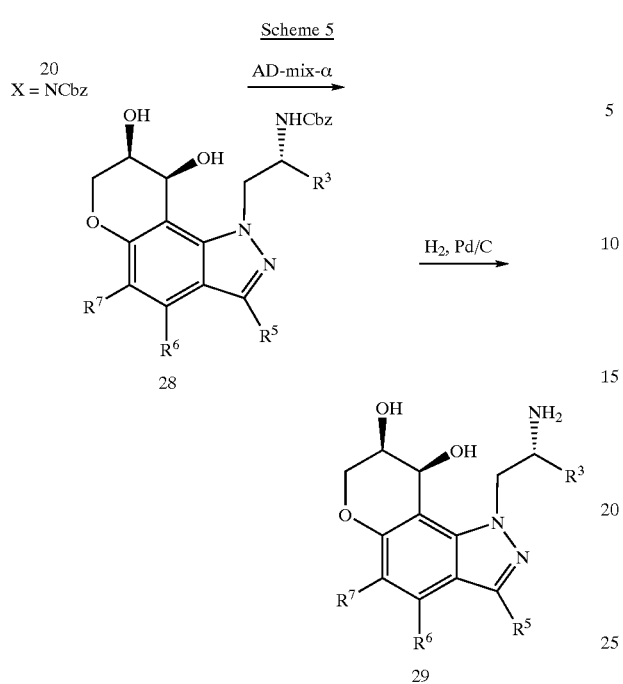

The 1-(hydroxyalkyl)-indazoles of interest for the preparation of compounds of Formula I can be prepared as outlined in Scheme 6 and in co-pending U.S. patent application Ser. No. 60/295,427, incorporated in its entirety by reference herein. Reaction of the activated fluorophenol 30 with the appropriate amino alcohol 31, which, when A is nitrile, is reduced to provide the corresponding aldehyde 32. Nitrosation to provide 33 followed by reductive cyclization provides the 1-(hydroxyalkyl)-indazoles 34.

Intermediate pyranoindazoles 34 can also be prepared by alkylation of the appropriate O-protected 6-hydroxy-indazole (35), where suitable O-protective groups are e.g. methyl or benzyl, by methods well known in the art and described in Scheme 7 [U.S. Pat. No. 5,494,928 (1997), WO98/30548 (1998)], with the desired epoxide, e.g. propylene oxide. Alternately, it can be advantageous for the preparation of certain compounds to alkylate 35 using chloroacetone followed by reduction, e.g. with $NaBH_4$, of the intermediate ketone to obtain the intermediate 34.

Scheme 7

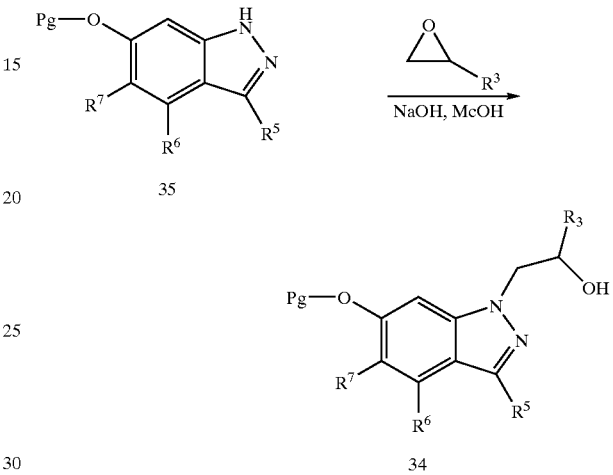

It can be advantageous to prepare certain compounds of Formula I from a suitably substituted 1,7,8,9-tetrahydro-pyrano[2,3-g]indazole, such as 36 as outlined in Scheme 8. For example, alkylation of 36 according to the conditions described for Scheme 4 above, followed by suitable activa-

Scheme 6

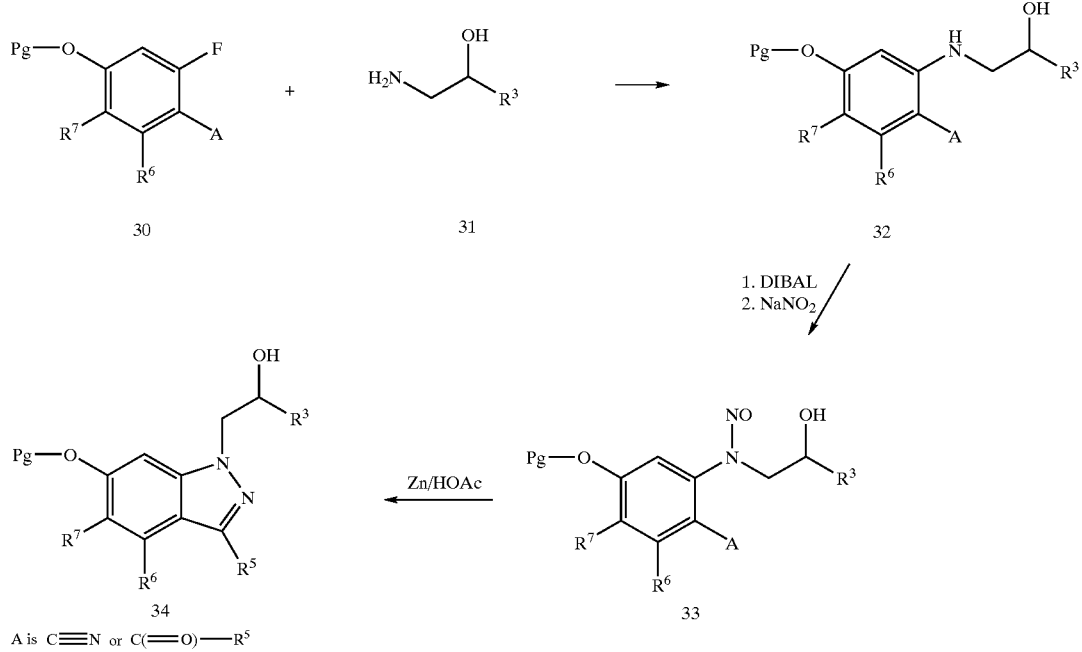

tion of the hydroxyl group toward subsequent nucleophilic amination by formation of a sulfonate ester [J. Chem. Soc., Perkins Vol. 1:1479, 1981], e.g. methanesulfonyl, toluenesulfonyl, bromophenylsulfonyl, or nitrophenylsulfonyl, and reaction with the desired amine provides compounds 38 of Formula I.

butyloxycarbonyl)amino]-cyclopropyl-1-methanol [J. Med. Chem., Vol. 31:1694, 1988], or 2-methyl-2-nitro-propan-1-ol [J. Amer. Chem. Soc., Vol. 68:12, 1946] would, following removal of the N-protective groups in the first three cases, or reduction of the nitro group in the latter, provide yet other examples 38 of Formula I.

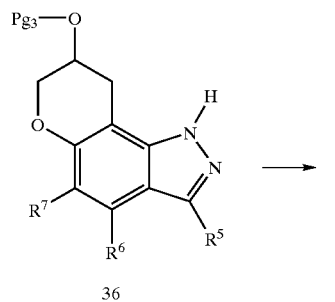

Scheme 8

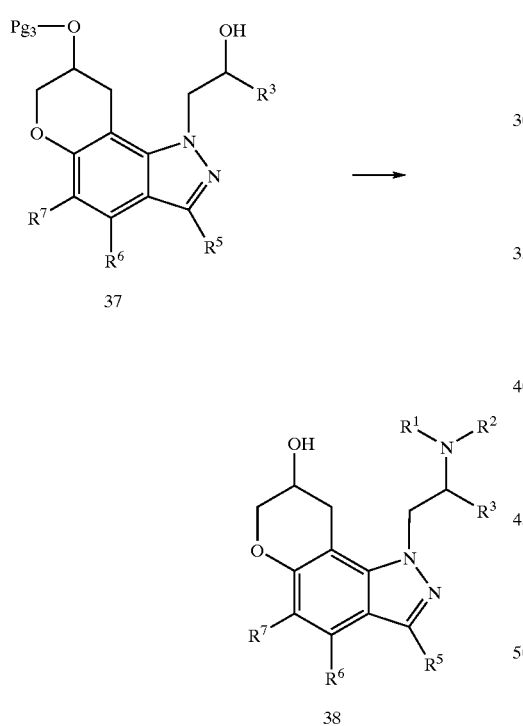

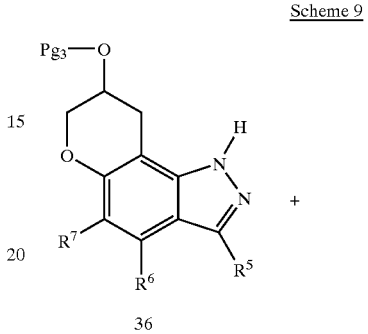

Scheme 9

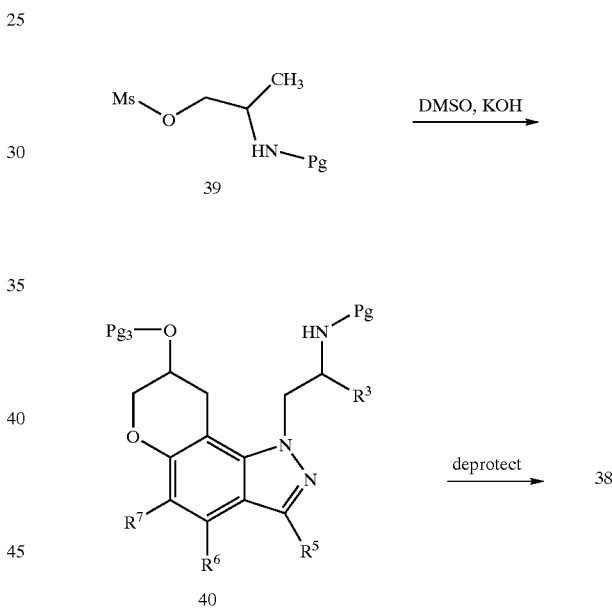

Furthermore, reaction of indazoles 36 with the activated alaninol 39 provides 40, which following deprotection gives compounds 38 of Formula I as shown in Scheme 9. Replacement of 39 in Scheme 9 with, for example, an activated sulfonate ester, or the corresponding halide, or N-protected (e.g. with t-butyloxycarbonyl, benzyloxycarbonyl) pyrrolidin-3-methanol would, following removal of the amine protective group, provide yet another compound of Formula I. Further, replacement of 39 in Scheme 9 with an activated sulfonate ester of N-(2-hydroxy-1,1-dimethyl-ethyl)-phthalimide [J. Amer. Chem. Soc., Vol. 108:3811, 1986], 2-[(t-butyloxycarbonyl)amino]-2-methylpropanol [J. Amer. Chem. Soc. Vol. 113:8879, 1991], 1-[(t-

Certain desirable substituted 1,7,8,9-tetrahydro-pyrano[2,3-g]indazoles can be prepared from the appropriately substituted 1H-indazol-6-ol (41), as described in the synthetic sequence outlined in Scheme 10. Alkylation of indazoles 41 with allyliodide followed by treatment under Claisen rearrangement conditions provides 43. Protection of the hydroxyl group from further reaction by conversion to, for example an ester such as acetyl, and similar incorporation of a protective group on the nitrogen atom, for example by reaction with a suitable isocyanide to give a ureide, provides the desired allyl indazole 45. Epoxidation of the olefin with, for example 3-chloro-perbenzoic acid, and subsequent cyclization under basic conditions, provides the pyranoindazole intermediate 47. Conversion of the hydroxyl group of pyranoindazole 47 into yet other functional groups consistent with Formula I can be accomplished by the application of functional group transformations well known in the art.

Scheme 10

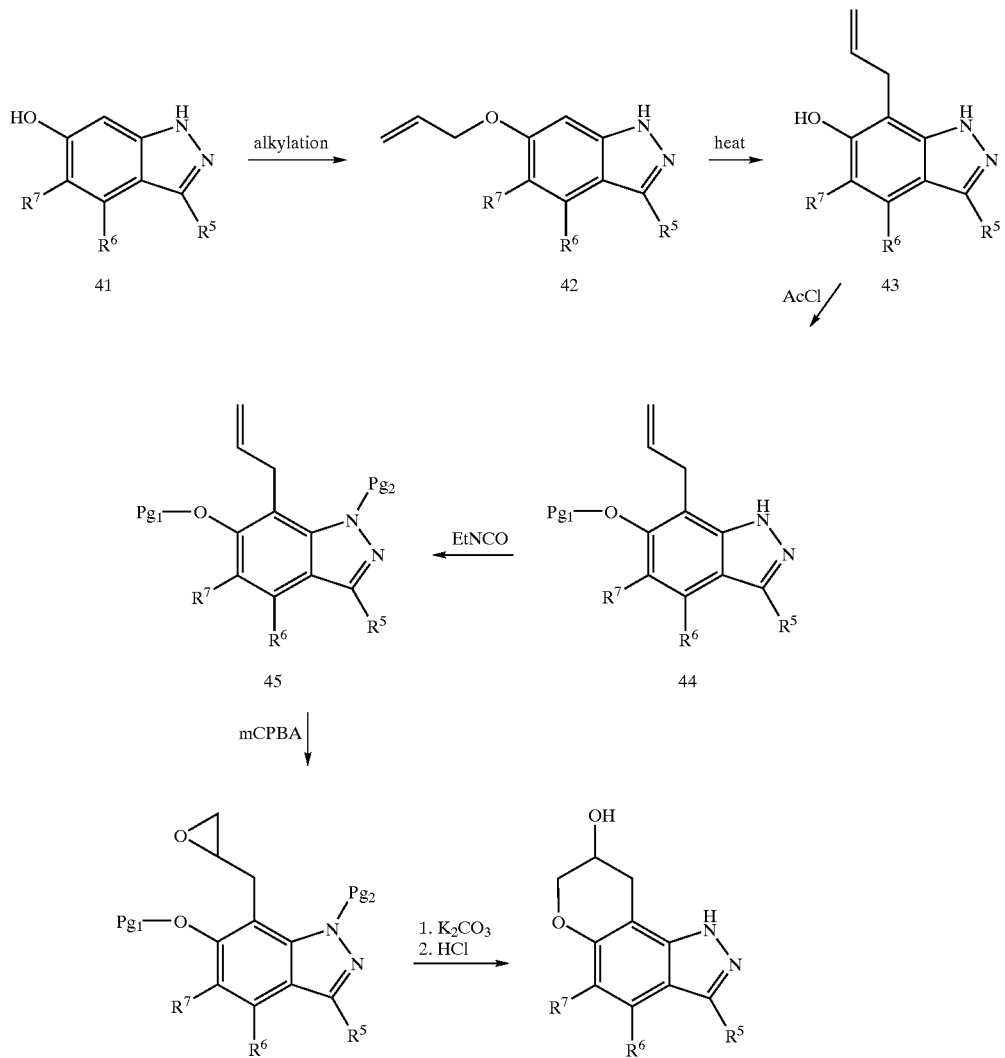

The desired pyrano[3,2-e]indazol-3-ethylamines 49 (Scheme 11) of Formula I can be prepared from the appropriately substituted 3-(2-hydroxypropyl)-1H-indazol-5-ol 48 by the methods described in Schemes 1 and 3 and as described in International Patent Application No. PCT/US00/31143, incorporated in its entirety by reference herein.

Scheme 11

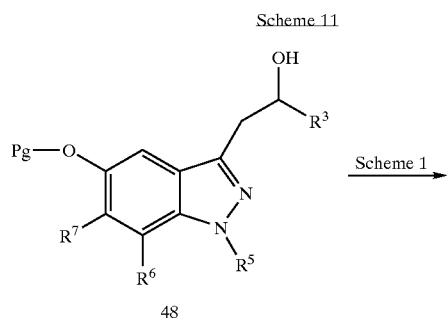

-continued

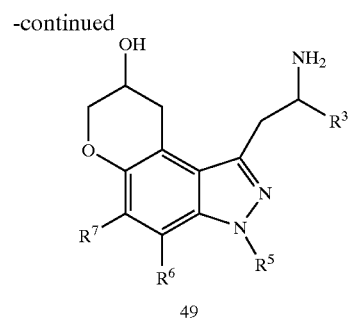

The compounds of the present invention can be used to lower and control IOP including IOP associated with normotension glaucoma, ocular hypertension, and glaucoma in warm blooded animals including humans. Since the treatment of glaucoma is preferably with compounds that do not enter the CNS, relatively polar compounds that are 5-HT$_2$ agonists are of particular interest. The compounds are preferably formulated in pharmaceutical compositions which are preferably suitable for topical delivery to the eye of the patient.

The compounds of this invention, Formula I, can be incorporated into various types of pharmaceutical compositions, such as ophthalmic formulations for delivery to the eye (e.g., topically, intracamerally, or via an implant). The compounds are preferably incorporated into topical ophthalmic formulations for delivery to the eye. The compounds may be combined with ophthalmologically acceptable preservatives, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity, such as hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-974, or the like, according to the published formulations for analogous ophthalmic preparations; preservatives and tonicity agents can be incorporated.

The compounds are preferably formulated as topical ophthalmic suspensions or solutions, with a pH of about 5 to 8. The compounds will normally be contained in these formulations in an amount 0.01% to 5% by weight, but preferably in an amount of 0.25% to 2% by weight. Thus, for topical presentation 1 to 2 drops of these formulations would be delivered to the surface of the eye 1 to 4 times per day according to the discretion of a skilled clinician.

The compounds can also be used in combination with other agents for treating glaucoma, such as, but not limited to, β-blockers (e.g., timolol, betaxolol, levobetaxolol, carteolol, levobunolol, propranolol), carbonic anhydrase inhibitors (e.g., brinzolamide and dorzolamide), $\alpha_1$ antagonists (e.g., nipradolol), $\alpha_2$ agonists (e.g. iopidine and brimonidine), miotics (e.g., pilocarpine and epinephrine), prostaglandin analogs (e.g., latanoprost, travaprost, unoprostone, and compounds set forth in U.S. Pat. Nos. 5,889,052; 5,296,504; 5,422,368; and 5,151,444, "hypotensive lipids" (e.g., lumigan and compounds set forth in U.S. Pat. No. 5,352,708), and neuroprotectants (e.g., compounds from U.S. Pat. No. 4,690,931, particularly eliprodil and R-eliprodil, as set forth in a pending application U.S. Ser. No. 06/203,350, and appropriate compounds from WO 94/13275, including memantine.

In the formulas described above, the alkyl group can be straight-chain, branched or cyclic and the like. Halogen includes Cl, Br, F, or I. Alkoxy is understood as an alkyl group bonded through an oxygen atom.

The compounds of the present invention preferably function as 5-$HT_2$ agonists and preferably do not enter the CNS. In more detail, the particular compounds of the present invention have incorporated into their structure a phenolic hydroxyl group which is considered comparable to that of serotonin and thus the compounds of the present invention preferably do not cross the blood-brain barrier and enter the brain. Compounds having the ability to be a 5-$HT_2$ agonist are beneficial for controlling IOP as well as the treatment of glaucoma as shown in International Published Patent Application No. WO 00/16761, incorporated in its entirety by reference herein.

The compounds of the present invention preferably provide increased chemical stability and preferably achieve the desired level of therapeutic activity which includes a lowering or controlling of IOP.

The compounds of the present invention can be used in controlling or lowering IOP in warm blooded animals including humans. Preferably, an effective amount of the compound is administered to the patient such that the IOP is controlled or lowered to acceptable levels. Furthermore, the compounds of the present invention can be used to treat glaucoma in warm blooded animals, including humans, by administering an effective amount of the compound to a patient in need of such treatment to treat the glaucoma. Examples of suitable pharmaceutical acceptable amounts of the compounds of the present invention include those amounts shown in the Examples.

Another embodiment of the present invention is a method to activate or bind to serotonin receptors comprising administering an effective amount of at least one compound of the present invention to a patient using an amount effective to block or bind to serotonin receptors, such as, but not limited to, the dosage levels described herein.

The following examples are given to illustrate the preparation of compounds that are the subject of this invention but should not be construed as implying any limitations to the claims. The preferred compounds of Formula I are described in Examples 4, and 5. The most preferred compound is Example 4. The proton magnetic resonance spectrum of each compound of the Examples was consistent with the assigned structure.

METHOD 1

5-$HT_2$ Receptor Binding Assay

To determine the affinities of serotonergic compounds at the 5-$HT_2$ receptors, their ability to compete for the binding of the agonist radioligand [$^{125}$I]DOI to brain 5-$HT_2$ receptors is determined as described below with minor modification of the literature procedure [Neuropharmacology, 26, 1803 (1987)]. Aliquots of post mortem rat or human cerebral cortex homogenates (400 μL) dispersed in 50 mM Tris HCl buffer (pH 7.4) are incubated with [$^{125}$I]DOI (80 pM final) in the absence or presence of methiothepin (10 μM final) to define total and non-specific binding, respectively, in a total volume of 0.5 mL. The assay mixture is incubated for 1 hour at 23° C. in polypropylene tubes and the assays terminated by rapid vacuum filtration over Whatman GF/B glass fiber filters previously soaked in 0.3% polyethyleneimine using ice-cold buffer. Test compounds (at different concentrations) are substituted for methiothepin. Filter-bound radioactivity is determined by scintillation spectrometry on a beta counter. The data are analyzed using a non-linear, iterative curve-fitting computer program [Trends Pharmacol. Sci., 16, 413 (1995)] to determine the compound affinity parameter. The concentration of the compound needed to inhibit the [$^{125}$I]DOI binding by 50% of the maximum is termed the $IC_{50}$ or $K_i$ value.

METHOD 2

5-HT$_2$ Functional Assay: [Ca$^{2+}$]$_i$ Mobilization

The receptor-mediated mobilization on intracellular calcium ([Ca$^{2+}$]$_i$) was studied using the Fluorescence Imaging Plate Reader (FLIPR) instrument. Rat vascular smooth muscle cells, A7r5, were grown in a normal media of DMEM/10% FBS and 10 µg/mL gentamycin. Confluent cell monolayers were trypsinized, pelleted, and re-suspended in normal media. Cells were seeded in a 50 µL volume at a density of 20,000 cells/well in a black wall, 96-well tissue culture plate and grown for 2 days.

On the day of the experiment, one vial of FLIPR Calcium Assay Kit dye was re-suspended in 50 mL of a FLIPR buffer consisting of Hank's Balanced Salt Solution (HBSS), 20 mM HEPES, and 2.5 mM probenecid, pH 7.4. Cells were loaded with the calcium-sensitive dye by addition of an equal volume (50 µL) to each well of the 96-well plate and incubated with dye for 1 h at 23° C.

Typically, test compounds were stored at 25 µM in 50% DMSO/50% Ethanol solvent. Compounds were diluted 1:50 in 20% DMSO/20% Ethanol. For "hit" screening, compounds were further diluted 1:10 in FLIPR buffer and tested at a final concentration of 10 µM. For dose-response experiments, compounds were diluted 1:50 in FLIPR buffer and serially diluted 1:10 to give a 5- or 8-point dose-response curve.

The compound plate and cell plate were placed in the FLIPR instrument. At the beginning of an experimental run, a signal test was performed to check the basal fluorescence signal from the dye-loaded cells and the uniformity of the signal across the plate. The basal fluorescence was adjusted between 8000–12000 counts by modifying the exposure time, the camera F-stop, or the laser power. Instrument settings for a typical assay were the following: laser power 0.3–0.6 W, camera F-stop F/2, and exposure time 0.4 sec. An aliquot (25 µL) of the test compound was added to the existing 100 µL dye-loaded cells at a dispensing speed of 50 µL/sec. Fluorescence data were collected in real-time at 1.0 sec intervals for the first 60 secs and at 6.0 sec intervals for an additional 120 secs. Responses were measured as peak fluorescence intensity minus basal and where appropriate were expressed as a percentage of a maximum 5-HT-induced response. When the compounds were tested as antagonists against 10 µM 5-HT, they were incubated with the cells for 15 minutes prior to the addition of 5-HT.

The above procedures were used to generate the data shown in Table 1.

TABLE 1

5-HT$_{2A}$ Receptor Binding and Functional Data

| Example | IC$_{50}$, nM | EC$_{50}$, nM | Efficacy (E$_{max}$, %) |
|---|---|---|---|
| 3 | 2.19 | 145 | 85 |
| 4 | 2.25 | 65.3 | 92 |
| 5 | 3.44 | 226 | 70 |
| 6 | 6.56 | 175 | 87 |
| 7 | 3.73 | 194 | 85 |
| 8 | 0.686 | 90 | 85 |
| 9 | 0.274 | 41.4 | 91 |
| 5-HT | 0.941 | 64.2 | 101 |

TABLE 2

IOP Response in Conscious Cynomolgus Monkeys

| Example | Dose, µg | Baseline IOP (mmHg) | Percent IOP Reduction ± SEM Hours after Dose | | |
|---|---|---|---|---|---|
| | | | 1 | 3 | 6 |
| 4 | 300 | 35.1 | 7.68 ± 2.91 | 25.8 ± 3.53 | 30.2 ± 4.48 |
| 5 | 300 | 34.3 | 7.9 ± 4.06 | 17.3 ± 3.87 | 25.1 ± 4.76 |
| (R)-DOI | 100 | 31.9 | 11.0 ± 4.98 | 25.3 ± 2.97 | 34.4 + 4.98 |

PREPARATION 1

1,7,8,9-Tetrahydro-pyrano[2,3-g]indazol-8-ol

Step A: 6-Allyloxy-1H-indazole

To a solution of 1H-indazol-6-ol (20.0 g, 150 mmol) in acetone (450 mL) was added pulverized potassium carbonate (22.4 g, 162 mmol), cesium carbonate (2.00 g, 5.7 mmol), and allyl iodide (14.63 mL, 160 mmol) and the mixture was stirred for 18 h at ambient temperature. Additional potassium carbonate (5.00 g, 36 mmol) and allyl iodide (1.4 mL, 15 mmol) were added and the mixture was stirred for 2 h followed filtration. Water (200 mL) was added to the filtrate and the volume of the mixture was reduced by about half in vacuo and extracted with dichloromethane (2×100 mL). The combined extracts were dried (MgSO$_4$) and evaporated to a residue which was purified by chromatography (silica, 20% to 50% EtOAc/hexane) to give a yellow solid (14.7 g, 56%): mp 110–112° C.; LC/MS (+APCI) m/z 175 (M+H). Unreacted starting material was recovered (4.71 g).

Step B: 7-Allyl-1H-indazol-6-ol

A solution of the product from Step A (14.2 g, 82 mmol) in 1,2-dichlorobenzene (90 mL) was fluxed for 6 h and the reaction mixture was evaporated to a residue which was purified by chromatography (silica, EtOAc) to give a tan solid (8.59 g, 60%) that was used in the next step: LC/MS (+APCI) m/z 175 (M+H).

Step C: Acetic acid 7-allyl-1H-indazol-6-yl ester

A solution of the product from Step B (6.35 g, 37 mmol) in THF (100 mL) containing triethylamine (7.6 ml, 55 mmol) was stirred for 5 minutes at ambient temperature, cooled to 0° C. (ice bath), and acetyl chloride (2.63 mL, 37 mmol) was added. The mixture was stirred at 0° C. for 2 hours, additional acetyl chloride (0.26 mL, 3.7 mmol) was added, and the mixture stirred for 10 min at which point another portion of acetyl chloride (0.26 ml, 3.7 mmol) was added and stirring continued for 15 min. The reaction was quenched with triethyl amine (1 mL) and saturated aqueous sodium bicarbonate (100 mL) and extracted with ethyl acetate (100 mL). The extract was dried (MgSO$_4$) and evaporated to an oil (9.27 g) which was purified by chromatography (silica, 10% to 50% EtOAc/hexane) to give a white solid, (3.50 g, 44%): LC/MS (+APCI) m/z 217 (M+H).

Step D: Acetic Acid 7-allyl-1-ethylcarbamoyl-1H-indazol-6-yl ester

To a solution of the product from Step C (2.5 g, 11.6 mmol) in THF (10 mL) was added ethylisocyanate (1.01 ml, 13 mmol) and the mixture heated at 70° C. for 18 h. The reaction mixture was evaporated to a residue which was purified by chromatography (silica, 10% to 50% EtOAc/hexane) to give a colorless oil (2.70 g, 81%): LC/MS (+APCI) m/z 288 (M+H).

Step E: Acetic acid 1-ethylcarbamoyl-7-oxiranylmethyl-1H-indazol-6-yl ester

To a solution of the product from Step D (2.70 g, 9.4 mmol) in dichloromethane (15 mL) was added 3-chloro-perbenzoic acid (2.31 g, 10.3 mmol, 77% pure) and the mixture stirred at ambient temperature for 1 h. Additional 3-chloro-perbenzoic (0.2 g, 0.9 mmol) was added and the reaction continued for 3 h. The reaction was quenched with saturated aqueous sodium bicarbonate (100 mL) and extracted with dichloromethane (50 mL). The extract was dried (MgSO$_4$) and evaporated to a white solid (1.59 g, 56%): mp 110–111° C.; LC/MS (+APCI) m/z 304 (M+H).

Step F: 1,7,8,9-Tetrahydro-pyrano[2,3-g]indazol-8-ol

To a solution of the product of Step E (1.44 g, 4.75 mmol) in methanol (100 mL) was added saturated aqueous potassium carbonate (10 mL) and the mixture stirred for 18 h at ambient temperature. Water (200 mL) was added to the reaction mixture and the pH adjusted to 7 with conc HCl followed by extraction ethyl acetate (5×100 mL). The combined extracts were dried (MgSO$_4$) and evaporated to tan solid (0.84 g, 93%): $^1$H NMR (DMSO-d$_6$) δ 12.77 (s, 1H), 7.94 (s, 1H), 7.49 (d, J=6.0 Hz, 1H), 6.66 (d, J=6.0 Hz, 1H), 5.02 (t, J=6.0 Hz, 1H), 4.85–4.95 (m, 1H), 3.62 (m, 2H), 2.9–3.4 (m, 2H); LC/MS (+APCI) m/z 191 (M+H).

PREPARATION 2

1-(6-Benzyloxyindazol-1-yl)-propan-2-ol

Step A: (6-Benzyloxy-indol-1-yl)-propan-2-ol

To a stirred, cooled (10° C.) suspension of sodium hydride (80.7 g of a 60% dispersion in mineral oil, 2.02 mol) in anhydrous THF (1.9 L) was added a solution of 6-benzyloxyindole (375 g, 1.68 mol) in anhydrous THF (1.9 L) keeping the temperature below 25° C. After 2 h at 10° C., propylene oxide (140 mL, 2.0 mol) was added dropwise keeping the temperature below 25° C. After 48 h at 10° C., propylene oxide (71 mL, 1.0 mol) was added. After 96 h at 10° C., saturated aqueous potassium dihydrogenphosphate (3.8 L) and ethyl acetate (3.8 L) were carefully added, the layers were separated and the aqueous solution was extracted with 3.8 L of ethyl acetate. The combined organic extracts were dried over sodium sulfate and concentrated in vacuo to yield a solid (520 g, 110%, contains mineral oil).

Step B: N-(5-Benzyloxy-2-formylphenyl)-N-(2-hydroxypropyl)-formamide

A solution of the product from Step A (172 g) in 1.5 L of dichloromethane was cooled to −78° C. and ozonized (4% ozone in oxygen). Excess ozone was displaced with oxygen for 5 min, followed by addition of dimethyl sulfide (78 mL) and warming to 25° C. The solution was concentrated to half volume, eluted through Florisil rinsing with ethyl ether-ethyl acetate and concentrated in vacuo. This procedure was repeated four times: one 172 g batch and three 58 g batches. The combined products were passed through silica (2.5 kg) with a gradient of 10%–80% ethyl acetate-hexane to yield, after concentration in vacuo, an oil (351 g, 70%).

Step C: 4-Benzyloxy-2-(2-hydroxy-propylamino) benzaldehyde

An ice-cooled solution of the product from Step B (298 g, 0.95 mol) in THF (3 L) was treated with 1 M aqueous sodium hydroxide (1.95 L, 1.9 mol) keeping the temperature below 8° C. After the starting material was consumed, the mixture was diluted with brine and extracted twice with ethyl ether. The organic solution was washed with water until neutral and then with brine, dried over sodium sulfate, treated with charcoal and passed through silica (1 kg) with ether and with 1:1 ethyl acetate-hexane to yield, after concentration in vacuo, a yellow solid (207 g, 76%).

Step D: 1-(6-benzyloxy-indazol-1-yl)-propan-2-ol

The product of Step C (202.7 g, 0.71 mol) was treated as described for Steps C and D of Preparation 3. After the nitrosamine intermediate had been converted to a mixture of the desired indazole product and unreacted starting material (5:1), sodium nitrite (29.5 g, 0.43 mol) was added to renitrosate the starting material. Zinc dust (84 g, 1.28 mol) was then added in portions with cooling as described. When the starting material was consumed, the reaction mixture was worked up as described and combined with the product from another batch that started with 176 g of the product of Step C. The combined crude products were purified by chromatography (Biotage Kiloprep-250) to give a solid (226 g, 60%): 99% purity by HPLC.

PREPARATION 3

(R)-1-(6-Benzyloxyindazol-1-yl)-propan-2-ol

Step A: 4-Benzyloxy-2-fluorobenzonitrile

Benzyl bromide (467 mL, 3.93 mol) and potassium carbonate (1.4 kg, 10.1 mol) were added to a solution of 2-fluoro-4-hydroxybenzonitrile (490 g, 3.57 mol) in acetone (3.4 L). The stirred mixture was heated at 60° C. for 20 h, then cooled and filtered. The filtrate was concentrated and the resulting solid was triturated with 10% ethyl acetate-hexane (5 L) and vacuum dried at 35° C. to give the desired product (787 g, 97%).

Step B: 4-Benzyloxy-2-((R)-2-hydroxy-propylamino) benzonitrile

A solution of (R)-(−)-1-amino-propan-2-ol (389 g, 5.19 mol) in dimethyl sulfoxide (600 mL) was added to a solution of the product from Step A (786 g, 3.46 mol), basic alumina (786 g), and 4 Å molecular sieves (131 g). The stirred mixture was heated at 110–140° C. for 24 h, cooled and filtered, the filter-aide was washed with 10 L of 4:1 ether-ethyl acetate followed by 4 L of 3:2 ethyl acetate-hexane. The organic washes were extracted with water (5 L) and the aqueous phase was extracted with 25% ethyl acetate-hexane (4×2 L). The combined organic phases were washed with water and brine, dried over sodium sulfate, concentrated to about 3 L and allowed to stand for 48 h. The precipitated solid was collected by filtration, washed with hexane, and vacuum-dried to provide the desired product in two crops (619 g and 86 g). The concentated supernatant was applied to a 5 kg silica gel pad and eluted with a gradient of 10–50% ethyl acetate-hexane to give, after concentration in vacuo, additional product (119 g): total yield was 791 g (81%).

Step C: 4-Benzyloxy-2-((R)-2-hydroxy-propylamino) benzaldehyde

Sodium hypophosphite hydrate (986 g, 11.2 mol) and Raney nickel (500 g of a 50% aqueous suspension) were added to a solution of the product from Step B (790 g, 2.8 mol) in a 2:1:1 mixture of pyridine-acetic acid-water (7 L). The mixture was stirred at 45° C. for 7 h, then cooled to 25° C. overnight and filtered through a filter-aide rinsing with water and ethyl acetate. The filtrate was washed with saturated sodium hydrogenphosphate to pH 5, water and brine, dried over sodium sulfate and concentrated. During concentration, 4 L of heptane was added to azeotropically remove pyridine. After 8 L of solvent had been removed the product solidified. Heptane (5 L) was added and the solid was triturated, isolated by filtration and vacuum dried at 35° C. to yield the desired product (722 g, 90%).

Step D: (R)-1-(6-benzyloxy-indazol-1-yl)-propan-2-ol

Sodium nitrite (209 g, 3.03 mol) was added over 25 min to a stirred solution of the product from Step C (720 g, 0.2.53 mol) in acetic acid (5.6 L) and water (1.4 L), keeping the temperature below 25° C. The resulting solution of the nitrosamine intermediate was cooled in an ice bath, and zinc dust (595 g, 9.10 mol) was added in 25 g portions over 3.5 h, keeping the temperature below 35° C. Ethyl acetate (7 L) was added and the thick suspension was filtered through a sintered glass funnel, washing with ethyl acetate (7.5 L). To the filtrate containing a 5:1 mixture of the desired indazole product and regenerated starting material was added Girard's Reagent T (98 g, 0.58 mol). After stirring at 25° C. for 1 day, another 150 g (0.90 mol) of Girard's Reagent T was added. After 3 more days all of the starting material was consumed. The mixture was extracted twice with water, with aqueous sodium hydrogenphosphate to remove acetic acid, water and brine, dried over sodium sulfate, filtered through Florisil, and concentrated. The residue was passed through 5 kg of silica with 1:1 ethyl acetate-hexane. Appropriate fractions were combined and concentrated, and heptane (4 L) was added to precipitate the indazole product. The solid was collected by filtration, washed with 1:1 ethyl acetate-hexane and vacuum dried at 35° C. give a yellow solid (417 g, 58%): HPLC analysis: (R)-96.7%; (S)-0.3%; starting material 3%. Concentration of the supernatant afforded an additional 141 g (20%) of the desired product.

PREPARATION 4

(S)-1-(6-Benzyloxyindazol-1-yl)-propan-2-ol

Method 1. This S stereoisomer was prepared as described above for the preparation of racemic 1-(6-benzyloxyindazol-1-yl)-propan-2-ol, but using (S)-1-amino-2-propanol instead of the racemic aminoalcohol.

Method 2. Step A: 4-Benzyloxy-2-fluoro-benzonitrile

A mixture of 2-fluoro-4-hydroxybenzonitrile (15.0 g, 109 mmol), potassium carbonate (21.0 g, 152 mmol), and benzyl bromide (19.6 g, 115 mmol) in acetone (150 mL) under nitrogen was heated at 50° C. overnight. The solid was removed by filtration and the filtrate evaporated to a residue that was mixed with ethyl acetate (500 mL). This solution was washed with brine, dried, and evaporated to give an amorphous solid: (24.9 g, 100%).

Step B: 4-Benzyloxy-2-((S)-2-hydroxy-propylamino)-benzonitrile

A mixture of the product from Step A (24.8 g, 109 mmol), (S)-1-amino-2-propanol (12.3 g, 164 mmol), 4A molecular sieves (4.0 g), and basic alumina (32 g) in anhydrous dimethyl sulfoxide (100 mL) under nitrogen was heated at 95° C. for 40 h. The suspension was cooled to ambient temperature, filtered through a filter-aide that was washed with ethyl acetate (2×300 mL) and water (300 mL). The aqueous layer of the filtrate was extracted with ethyl acetate (2×300 mL) and the combined organics were washed with brine (200 mL), dried (MgSO$_4$), and purified by chromatography (silica, EtOAc/hexane) to give a viscous oil (24.9 g, 81%).

Step C: 4-Benzyloxy-2-((S)-2-hydroxy-propylamino)-benzaldehyde

To a solution of the product of Step B (19.3 g, 68.3 mmol) in a mixture of anhydrous cyclohexane and THF (200 mL, 40 mL) at 0° C. under nitrogen was added diisobutylammonium hydride (1 M solution in hexane, 239 mL, 239 mmol) over 30 min. This mixture was stirred 18 h at ambient temperature, additional diisobutylammonium hydride (40 mL, 40 mmol) was added, and the mixture was stirred an additional 24 h. The reaction mixture was cooled on an ice bath and the reaction was quenched by the addition of MeOH (exothermic) and 2 N HCl to maintain a pH of 1. The mixture was extracted with EtOAc (3×300 mL) and the extracts were dried and concentrated to a brown oil (18.5 g). The crude oil was triturated with EtOAc/hexane, and filtered to give an oil (16.1 g, 83% crude yield). A small portion of this material was purified by chromatography (silica, 20% to 50% EtOAc/hexane) to afford a solid; mp 68–69° C.

Step D: (S)-1-(6-Benzyloxyindazol-1-yl)-propan-2-ol (4)

To a mixture of the product from Step C (16.0 g, 56.1 mmol) in acetic acid/water (150 mL/30 mL) at 0° C. was added sodium nitrite (7.75 g, 112 mmol) in portions over 40 min. The mixture was stirred for 50 min, cooled (ice bath), and zinc (14.7 g, 224 mmol) was added in portions. After 1 h the suspension was warmed to room temperature and more zinc was added (14.7 g, 224 mmol). The mixture was stirred for 1 h, concentrated, and extracted with EtOAc (2×300 mL). The extracts were filtered through a filter-aide, and the filtrate was washed with saturated aqueous disodium hydrogen phosphate (to pH 8) and brine, dried, and purifed by chromatrography (silica, 25% EtOAc/hexane) to afford an oil (7.01 g, 44%).

EXAMPLE 1

1-(2-Aminopropyl)-1,7,8,9-tetrahydro-pyrano[2,3-g]indazol-8-ol

Step A: 6-Benzyloxy-1-[2-(tert-butyldimethyl-silanyloxy)-propyl]-1H-indazole

To a mixture of 1-(6-benzyloxyindazol-1-yl)-propan-2-ol (10 g, 35.5 mmol) in THF (100 mL) and imidazole (3.4 g, 50 mmol) was added tert-butyl-chloro-dimethyl-silane (6.42 g, 42.6 mmol) and the mixture was stirred for 15 min at ambient temperature. The reaction mixture was poured into a saturated aqueous solution of ammonium acetate (300 mL) and extracted with ethyl acetate (2×150 mL). Purification by chromatography (silica, EtOAc/hexane) gave a yellow solid (10.6 g, 76%): mp 56–58° C.; LC/MS (+APCI) m/z 397 (M+H).

Step B: 1-[2-(tert-Butyldimethyl-silanyloxy)-propyl]-1H-indazol-6-ol

A mixture of the product from Step A (10.6 g, 27 mmol) and palladium-on-carbon (10%, 0.26 g) in methanol (250 mL) was stirred under an atmosphere of hydrogen for 6 h, dichloromethane (100 mL) was added and the mixture filtered. Evaporation of the filtrate gave an off-white solid (7.0 g, 85%): mp 169–174° C.; LC/MS (+APCI) m/z 307 (M+H).

Step C: 7-Bromo-1-[2-(tert-butyldimethyl-silanyloxy)-propyl]-1H-indazol-6-ol

To a solution of the product from Step B (6.00 g, 19.6 mmol) in anhydrous THF (300 mL) at 0° C. was added N-bromosuccinimide (3.49 g, 19.6 mmol) in 10 portions over 20 min. The mixture was poured into a saturated aqueous solution of sodium bisulfite (300 mL) and extracted with EtOAc (3×100 mL). The combined extracts were dried (MgSO$_4$) and evaporated to a residue (6.39 g). Chromatography (silica, 10% EtOAc/hexane) gave a solid (4.95 g, 66%): LC/MS (+APCI) m/z 385, 387 (M+H).

Step D: 7-Bromo-1-[2-(tert-butyldimethyl-silanyloxy)-propyl]-6-oxiranylmethoxy-1H-indazole A suspension of the product from Step C (4.47 g, 11.6 mmol), potassium carbonate (2.25 g, 16 mmol), and epibromohydrine (1.59 mL, 19 mmol) in acetone (230 mL) was heated at reflux for 20 h. Additional epibromohydrine (1.5 mL, 17.9 mmol) was added and the mixture heated at reflux for 18 h. The solid was removed by filtration and the filtrate was concentrated to an oil which was dissolved in EtOAc (150 mL). This solution was washed with saturated aqueous ammonium acetate (150 mL), dried (MgSO$_4$), and evaporated to a residue which was purified by chromatography (silica, 2% to 10% EtOAc/hexane) to afford an oil (3.77 g, 74%): LC/MS (+APCI) m/z 441, 443 (M+H).

Step E: 1-Bromo-3-[7-bromo-1-[2-(tert-butyl-dimethyl-silanyloxy)-propyl]-1H-indazol-6-yloxy]-propan-2-ol Dibromoethane (1.09 mL, 12.6 mmol) was added dropwise to a suspension of magnesium powder (0.81 g, 33.5 mmol) in anhydrous THF (150 mL) under nitrogen. During this period the mixture was heated at about 50° C. until gas evolution was observed and then allowed to cool to 40° C. Additional dibromoethane (0.05 mL) was added and the mixture was heated at reflux for 20 min and placed in an ice bath. To the cooled mixture was added a solution of the product from Step D (3.70 g, 8.38 mmol) in THF (50 mL). After stirring for 20 min at ambient temperature, the reaction was quenched with a saturated aqueous solution of ammonium chloride (200 mL) and the mixture was extracted with EtOAc (2×150 mL). Evaporation of the extracts gave a crude oil (3.78 g, 86%): LC/MS (+APCI) m/z 521, 523, 525 (M+H).

Step F: 7-Bromo-6-[3-bromo-2-(1-ethoxyethoxy)-propoxy]-1-[2-(tert-butyldimethyl-silanyloxy)-propyl]-1H-indazole To a solution of the product from Step E (3.78 g, 7.2 mmol) and p-toluenesulfonic acid (0.14 g) in dichloromethane (50 mL) at 0° C. was added ethyl vinyl ether (2.75 mL, 28.8 mmol). After 30 min the reaction was quenched with a saturated solution of sodium bicarbonate (50 mL) and the mixture was extracted with dichloromethane (3×80 mL). Evaporation and purification by chromatography (silica, 1% to 8% EtOAc/hexane) gave a viscous oil (3.30 g, 77%): LC/MS (+APCI) m/z 593, 595, 597 (M+H).

Step G: 1-[8-(1-Ethoxyethoxy)-8,9-dihydro-7H-pyrano[2,3-g]indazol-1-yl]-propan-2-ol To a solution of the product from Step F (3.3 g, 5.5 mmol) in anhydrous THF (100 mL) at −78° C. under nitrogen was added n-butyllithium lithium (2.5 M in hexanes, 2.76 mL, 6.90 mmol). After 30 min the reaction was quenched with a saturated solution of sodium bicarbonate (200 mL) and the mixture was extracted with EtOAC (2×150 mL). The combined extracts were dried (MgSO$_4$) and evaporated to give a residue that was chromatographed (silica, 10% EtOAC/hexane) to give an oil (1.06 g), which was dissolved in THF (50 mL); tetrabutylammonium fluoride (1 M solution in THF, 3.84 mL, 13.8 mmol) was added to this solution. The mixture was stirred overnight at ambient temperature, poured into a saturated solution of sodium bicarbonate (200 mL), and extracted with EtOAc (2×100 mL). The combined extracts were dried (MgSO$_4$), evaporated, and chromatographed (silica, 20% to 50% EtOAc/hexane) to give an oil (0.52 g, 29%): LC/MS (+APCI) mz 321 (M+H).

Step H: 1-(2-Azidopropyl)-8-(1-ethoxyethoxy)-1,7,8,9-tetrahydro-pyrano[2,3-g]indazole To solution of the product from Step G (0.52 g, 1.6 mmol) and triethylamine (1.12 mL, 8.1 mmol) in anhydrous THF (75 ml) at 0° C. was added methanesulfonic anhydride (0.71 g, 4.05 mmol). The mixture was stirred for 20 min and sodium azide (2.11 g, 32.4 mmol) was added along with DMSO (20 mL). The THF was removed (in vacuo) and the reaction mixture was heated at 90° C. for 3 h. The mixture was cooled, poured into a saturated solution of sodium bicarbonate (150 mL), and extracted with EtOAc (3×100 mL). The combined extracts were washed with brine (100 mL), dried (MgSO$_4$), and evaporated to a residue that was purified by chromatography (silica, 10% EtOAc/hexane) to give an oil (0.40 g, 72%): LC/MS (+APCI) mz 346 (M+H).

Step I: 1-(2-Azidopropyl)-1,7,8,9-tetrahydro-pyrano[2,3-g]indazol-8-ol

To a mixture of the product from Step H (0.40 g, 1.1 mmol) in THF (60 mL) was added 1 N HCl (26 mL). After stirring for 40 min a saturated solution of sodium bicarbonate (150 mL) was added and the mixture was extracted with EtOAc (3×100 mL). The combined extracts were dried and evaporated to a residue, which was purified by chromatography (silica, 50% EtOAc/hexane) to give an oil (0.29 g, 92%): LC/MS (+APCI) m/z 374 (M+H).

Step J: 1-(2-Aminopropyl)-1,7,8,9-tetrahydro-pyrano[2,3-g]indazol-8-ol hydrochloride A mixture of the product from Step 1 (0.27 g, 0.99 mmol) and palladium-on-carbon (10%, 0.03 g) in EtOH (20 mL) was stirred under an atmosphere of hydrogen for 18 h at ambient temperature. The mixture was filtered and the filtrate evaporated to a residue which was dissolved in EtOAc/hexane (1:1) (10 mL). After standing for 18 h the precipitate was collected as a colorless solid (0.14 g, 57%): mp 124–125° C.; LC/MS (+APCI) mz 248 (M+H). Analysis. Calculated for $C_{13}H_{17}N_3O_2 \cdot 0.33H_2O$: C, 61.64; H, 7.03; N, 16.59. Found: C, 61.62; H, 6.83; N, 16.43.

EXAMPLE 2

1-((R)-2-Aminopropyl)-1,7,8,9-tetrahydro-pyrano[2,3-g]indazol-8-ol hydrochloride Step A: 6-Benzyloxy-1-[(S)-2-(tert-butyldimethyl-silanyloxy)-propyl]-1H-indazole To a mixture of (S)-1-(6-benzyloxyindazol-1-yl)-propan-2-ol (2.03 g, 7.20 mmol) in anhydrous THF/DMF (100 mL/35 mL) under nitrogen was added sodium hydride (60% in mineral oil, 0.40 g, 10.0 mmol). After 30 min tert-butyl-chloro-dimethyl-silane (1.52 g, 10 mmol) and a catalytic amount of NaI were added and the mixture was stirred overnight at ambient temperature. Additional NaH (5 mmol) and tert-butyl-chloro-dimethyl-silane (5 mmol) were added to the reaction mixture, which was stirred for 6 h. The reaction mixture was evaporated to a residue that was mixed with a saturated aqueous solution of sodium bicarbonate and extracted with ethyl acetate (2×200 mL). Purification by chromatography (silica, EtOAc/hexane) gave an oil (2.81 g, 99%).

Step B: 1-[(S)-2-(tert-Butyldimethyl-silanyloxy)-propyl]-1H-indazol-6-ol

A mixture of the product from Step A (5.44 g, 13.7 mmol) and palladium-on-carbon (10%, 0.50 g) in methanol (200 mL) was stirred under an atmosphere of hydrogen for 18 h, filtered and evaporated to give an off-white solid (3.80 g, 90%): mp 171–172° C.

Step C: 7-Bromo-1-[(S)-2-(tert-butyldimethyl-silanyloxy)-propyl]-1H-indazol-6-ol To a solution of the product from Step B (3.79 g, 12.4 mmol) in anhydrous THF (100 mL) at 0° C. was added N-bromosuccinimide (2.20 g, 12.4 mmol) in 3 portions over 10 min. After 20 min the mixture was poured into a saturated aqueous solution of sodium bisulfite (100 mL) and extracted with EtOAc (3×200 mL). The combined extracts were dried (MgSO$_4$) and evaporated to a residue (4.79 g). Chromatography (silica, 10% EtOAc/hexane) gave a solid (3.66 g, 77%): mp 103–105° C.

Step D: 7-Bromo-1-[(S)-2-(tert-butyldimethyl-silanyloxy)-propyl]-6-oxiranylmethoxy-1H-indazole A suspension of the product from Step C (3.66 g, 9.51 mmol), potassium carbonate (1.92 g, 1.46 mmol), and epi-bromohydrine (1.32 mL, 1.60 mmol) in acetone (200 mL) was heated at reflux for 30 h. The solid was removed by filtration and the filtrate was concentrated to an oil that was purified by chromatography (silica, 2% to 10% EtOAc/hexane) to afford an oil (3.33 g, 79%): LC/MS (+APCI) m/z 441, 443 (M+H).

Step E: 1-Bromo-3-[7-bromo-1-[(S)-2-(tert-butyl-dimethyl-silanyloxy)-propyl]-1H-indazol-6-yloxy]-propan-2-ol To a suspension of magnesium powder (0.73 g, 30.2 mmol) in anhydrous THF (50 mL) under nitrogen was added dibromoethane (2.13 g, 0.98 mL, 11.3 mmol) in portions over about 30 min. During this period the mixture was heated at about 50° C. until gas evolution was observed. The mixture was stirred for an additional 1 h, placed in an ice bath, and a solution of the product from Step D (3.33 g, 7.55 mmol) in THF (10 mL) was added. After stirring for 1 h at ambient temperature, the mixture was quenched with a saturated aqueous solution of ammonium chloride (100 mL) and extracted with EtOAc (3×100 mL). Evaporation of the extracts gave a crude oil (3.76 g, 95%): LC/MS (+APCI) m/z 441, 443 (M+H−HBr).

Step F: 7-Bromo-6-[3-bromo-2-(1-ethoxyethoxy)-propoxy]-1-[(S)-2-(tert-butyldimethyl-silanyloxy)-propyl]-1H-indazole To a solution of the product from Step E (1.85 g, 3.54 mmol) and p-toluenesulfonic acid (0.01 g) in dichloromethane (50 mL) at 0° C. was added ethyl vinyl ether (1 mL, 10.5 mmol). After 30 min the reaction was quenched with a saturated solution of sodium bicarbonate (50 mL) and extracted with EtOAc (3×80 mL). Evaporation and purification by chromatography (silica, 1% to 8% EtOAc/hexane) gave a viscous oil (1.79 g, 81%): LC/MS (+APCI) m/z 595 (M+H).

Step G: (S)-1-[8-(1-Ethoxyethoxy)-8,9-dihydro-7H-pyrano[2,3-g]indazol-1-yl]-propan-2-ol To a solution of the product from Step F (0.90 g, 2.07 mmol) in anhydrous THF (50 mL) at −78° C. under nitrogen was added n-butyllithium lithium (2.5 M in hexanes, 1.56 mL, 3.90 mmol) over 3 min. After 30 min the reaction was quenched with a saturated solution of sodium bicarbonate (80 mL) and the mixture was extracted with EtOAc (3×100 mL). The combined extracts were dried ($MgSO_4$) and evaporated to give an oil (1.30 g) that was dissolved in THF (50 mL); tetrabutylammonium fluoride (1 M solution in THF) was added to this solution. The mixture was stirred overnight at ambient temperature, poured into a saturated solution of sodium bicarbonate (80 mL), and extracted with EtOAc (3×100 mL). The combined extracts was evaporated and chromatographed (silica, 10% to 40% EtOAc/hexane) to give an oil (0.35 g, 53%): LC/MS (+ES) m/z 321 (M+H).

Step H: 1-((R)-2-Azidopropyl)-8-(1-ethoxyethoxy)-1,7,8,9-tetrahydro-pyrano[2,3-g]indazole To a solution of the product from Step G (0.35 g, 1.09 mmol) and triethylamine (0.55 g, 5.47 mmol) in anhydrous THF (50 ml) at 0° C. was added methanesulfonic anhydride (0.47 g, 2.73 mmol). The mixture was stirred for 1 h and sodium azide (0.71 g, 10.9 mmol) was added. The reaction mixture was evaporated to a residue that was dissolved in anhydrous DMF (80 mL) and heated at 95° C. for 3 h. The mixture was cooled, poured into a saturated solution of sodium bicarbonate (80 mL), and extracted with EtOAc (3×80 mL). The combined extracts were dried ($MgSO_4$) and evaporated to a residue that was purified by chromatography (silica, 10% EtOAc/hexane) to give an oil (0.30 g, 80%): LC/MS (+APCI) m/z 346 (M+H).

Step I: 1-((R)-2-Azidopropyl)-1,7,8,9-tetrahydro-pyrano[2,3-g]indazol-8-ol

To a mixture of the product from Step H (0.30 g, 0.87 mmol) in THF (50 mL) was added 1 N HCl (20 mL). After stirring for 40 min a saturated solution of sodium bicarbonate (80 mL) was added and the mixture was extracted with EtOAc (3×50 mL). The combined extracts were dried and evaporated to a residue, which was purified by chromatography (silica, 20% to 50% EtOAc/hexane) to give an oil (0.22 g, 92%).

Step J: 1-((R)-2-Aminopropyl)-1,7,8,9-tetrahydro-pyrano[2,3-g]indazol-8-ol hydrochloride A mixture of the product from Step 1 (0.21 g, 0.77 mmol) and palladium-on-carbon (10%, 0.02 g) in MeOH (30 mL) was stirred under an atmosphere of hydrogen for 18 h at ambient temperature. The mixture was filtered and the filtrate was combined with a solution of hydrogen chloride in ethanol (2 N, 1 mL); this solution was evaporated at 60° C. under high vacuum to give a solid (0.13 g, 59%): mp 82–86° C.; LC/MS (+APCI) m/z 248 (M+H). Analysis. Calculated for $C_{13}H_{17}N_3O_2 \cdot HCl \cdot 0.1H_2O \cdot 0.4C_3H_7NO$: C, 54.17; H, 6.72; N, 15.12. Found: C, 54.06; H, 6.76; N, 14.98.

EXAMPLE 3

1-((S)-2-Aminopropyl)-1,7,8,9-tetrahydro-pyrano[2,3-g]indazol-8-ol

Step A: 1-((S)-2-Azidopropyl)-1,7,8,9-tetrahydro-pyrano[2,3-g]indazol-8-ol

This compound was synthesized by following the procedure described in Example 2, Step I but using 1-((S)-2-azidopropyl)-8-(1-ethoxyethoxy)-1,7,8,9-tetrahydro-pyrano[2,3-g]indazole, which was prepared from (S)-1-(6-benzyloxyindazol-1-yl)-propan-2-ol instead of (R)-1-(6-benzyloxyindazol-1-yl)-propan-2-ol as described: oil (0.45 g, 79%); LC/MS (+APCI) m/z 274 (M+H).

Step B: 1-((S)-2-Aminopropyl)-1,7,8,9-tetrahydro-pyrano[2,3-g]indazol-8-ol

A solution of the product from Step A in methanol was treated as described in Example 2, Step J to give the free base as an amorphous solid (0.36 g, 88%): mp 46–51° C.; GCMS(Cl+) m/z 248 (M+H). Analysis. Calculated for $C_{13}H_{17}N_3O_2 \cdot 0.1H_2O$: C, 62.68; H, 6.96; N, 16.97. Found: C, 62.55; H, 7.03; N, 16.64.

EXAMPLE 4

(R)-1-((S)-2-Aminopropyl)-1,7,8,9-tetrahydro-pyrano[2,3-g]indazol-8-ol

Step A. 1-[2-(R)-(tert-Butyl-dimethyl-silanyloxy)-propyl]-6-prop-2-ynyloxy-1H-indazole To a solution of 1-[(R)-2-tert-butyldimethylsilanyloxy)-propyl]-1H-indazol-6-ol [10.93 g, 35.7 mmol, prepared from (R)-1-(6-benzyloxyindazol-1-yl)propan-2-ol by the method of Example 2, Step B] in acetone (250 mL) was added potassium carbonate (6.90 g, 35.7 mmol) and propargyl bromide (5.19 mL, 46.4 mmol) and the mixture was heated at reflux for 18 h. Additional potassium carbonate (1.97 g, 14 mmol) and propargyl bromide (1.2 mL, 10.7 mmol) were added and the mixture refluxed for 2 hr. The solid was removed by filtration and the filtrate concentrated to an oil which was purified by chromatography (silica, 5% ethyl acetate in hexane) to afford an oil (1.40 g, 96%): LCMS (+APCI) m/z 345 (M+H).

Step B. 1-[(R)-2-(tert-Butyl-dimethyl-silanyloxy)-propyl]-1,7-dihydro-pyrano[2,3-g]indazole A solution of the product from Step A (10.9 g, 31.8 mmol) in mesitylene (60 mL) was placed in a pressure tube and degassed under vacuum. The tube was sealed and heated at 190° C. for 20 h. The solution was cooled and purified by chromatography (silica, 10% ethyl acetate in hexane) to give a solid (9.53 g, 87%): mp 58–59° C.; LC/MS (+APCI) m/z 345 (M+H).

Step C. (R)-1-[(R)-2-(tert-Butyl-dimethyl-silanyloxy)-propyl]-1,7,8,9-tetrahydro-pyrano[2,3-g]indazol-8-ol To the product of Step B (1.00 g, 2.91 mmol) was added 9-BBN (0.5 M in THF, 13 mL, 6.4 mmol) under nitrogen with stirring. The solution was heated at 70° C. for 2 h, cooled to ambient temperature and the reaction was quenched with methanol (5 mL) and hydrogen peroxide (30%, 5 mL). After stirring for 30 min the mixture was evaporated to a residue, which was combined with a saturated solution of sodium bicarbonate (50 mL) and this mixture was extracted with ethyl acetate (3×50 mL). The combined extracts were evaporated to a residue which was purified by chromatography (silica, 10% to 30% ethyl acetate in hexane) to give the desired diastereomer as a viscous oil (0.56 g, 75%) and a mixture (0.22 g) of unseparated diastereomers: LCMS (+APCI) m/z 363 (M+H).

Step D. (R)-1-((S)-2-Azido-propyl)-1,7,8,9-tetrahydro-pyrano[2,3-g]indazol-8-ol

A solution of the product of Step C (0.56 g, 1.55 mmol), pyridinium p-toluenesulfonate (50 mg) and ethyl vinyl ether (1 mL) in anhydrous dichloromethane (50 mL) under nitrogen at 0° C. was stirred for 1 hr. The cooling bath was removed and the mixture was stirred for 1 h and triethylamine (1 mL) was added. This mixture was evaporated to a residue, which was combined with THF (10 mL) and tetrabutylammonium fluoride (1 M solution in THF, 3.1 mL, 3.1 mmol) and stirred for 1 h. The reaction mixture was evaporated to a residue which was purified by chromatography (silica, 10% to 30% ethyl acetate in hexane) to give the hydroxy-ether intermediate as an oil (0.47 g, 96%). To a solution of this oil (0.46 g, 1.44 mmol) in anhydrous THF (50 mL) at 0° C. was added triethylamine (0.726 g, 7.19 mmol) and methanesulfonic anhydride (0.50 g, 2.88 mmol) and the mixture was stirred for 30 min. Sodium azide (0.936 g, 14.4 mmol) was added and the solvent was removed by evaporation. DMF (50 mL) was added and the suspension was heated at 100° C. for 4 h, cooled and extracted with ethyl acetate (3×80 mL). The combined extracts were washed with water, dried, and purified by chromatography (1% to 10% ethyl acetate in hexane) to give the azido-ether as an oil (0.38 g, 77%). The oil was dissolved in methanol (10 mL) and p-toluenesulfonic acid (50 mg) was added; this solution was stirred for 1 h. Triethylamine (0.1 mL) was added and the mixture was evaporated to a residue, which was purified by chromatography (10% to 35% ethyl acetate in hexane) to give the desired azido-alcohol as a solid (0.27 g, 99%): LCMS (+APCI) m/z 274 (M+H).

Step E. (R)-1-((S)-2-Aminopropyl)-1,7,8,9-tetrahydro-pyrano[2,3-g]indazol-8-ol

The product from Step D was treated as described in Step J of Example 2 to give the desired compound as a yellowish solid (0.26 g, 65%): mp 126–128° C.; $[\alpha]_D$=+47.7° (c 0.352, $CH_3OH$); $[\alpha]_{405}$=+115° (c 0.352, $CH_3OH$); LC/MS (+APCI) m/z 248 (M+H); Calculated for $C_{13}H_{17}N_3O_2$: C, 63.14; H, 6.93; N, 16.99. Found: C, 63.37; H, 6.79; N, 16.93.

EXAMPLE 5

(S)-1-((S)-2-Aminopropyl)-1,7,8,9-tetrahydro-pyrano[2,3-g]indazol-8-ol

Step A: (S)-1-((S)-2-Azido-propyl)-1,7,8,9-tetrahydro-pyrano[2,3-g]indazol-8-ol

The product from Example 3, Step A (1.35 g) was applied to a chromatography column packed with chiral adsorbant (Chiracel OJ). Elution with a mixture of hexane and 2-propanol (9:1) afforded separation of the mixture to provide the two diastereomers: S,8S-diastereomer (0.68 g) and the S,8R-diastereomer (0.65 g).

Step B: (S)-1-((S)-2-Aminopropyl)-1,7,8,9-tetrahydro-pyrano[2,3-g]indazol-8-ol

A solution of the S,8S-diastereomer (0.23 g) from Step A in methanol was treated as described in Example 3, Step B to give an oil (0.18 g, 87%): $[\alpha]_D$=−6.21° (c 0.467, $CH_3OH$); $[\alpha]_{405}$=−3.5° (c 0.467, $CH_3OH$). Analysis. Calculated for $C_{13}H_{17}N_3O_2 \cdot 0.2H_2O$: C, 62.22; H, 7.03; N, 16.74. Found: C, 62.36; H, 7.06; N, 16.93.

EXAMPLE 6

(R)-1-((S)-2-Amino-propyl)-1,7,8,9-tetrahydro-pyrano[2,3-g]indazol-8-ylamine trihydrochloride Step A: (S)-8-Azido-1-((R)-2-azido-propyl)-1,7,8,9-tetrahydro-pyrano[2,3-g]indazole To a solution of the S,8S-diastereomer of Example 5, Step A (0.44 g, 1.61 mmol) and triethylamine (0.90 mL, 6.44 mmol) in anhydrous THF (50 mL) at 0° C. was added methanesulfonic anhydride (0.56 g, 3.22 mmol); this mixture was stirred for 30 min, the ice bath was removed, and the mixture was stirred for an additional 20 min. The reaction mixture was evaporated to a residue to which DMSO (50 mL) and sodium azide (1.05 g, 16.1 mmol) were added followed by heating at 90° C. for 5 h. The mixture was cooled, poured into water, and extracted with ethyl acetate (3×60 mL). The combined extracts were dried, filtered, and evaporated to dryness. Purification by chromatography (silica, 5% to 25% ethyl acetate in hexane) gave an oil (0.19 g, 66%): LC/MS (+APCI) m/z 299 (M+H).

Step B: (R)-1-((S)-2-Amino-propyl)-1,7,8,9-tetrahydro-pyrano[2,3-g]indazol-8-ylamine trihydrochloride A solution of the product from Step A in methanol was treated as described in Example 2, Step J to give a yellowish solid (0.16 g, 78%): mp>300° C.; LC/MS (+APCI) m/z 247 (M+H). Analysis. Calculated for $C_{13}H_{21}Cl_3N_4O \cdot 0.33C_2H_5OH \cdot 0.5H_2O$: C, 43.14; H, 6.35; N, 14.72. Found: C, 43.52; H, 6.39; N, 14.51.

EXAMPLE 7

(8R*,9S*)-1-((S)-2-Amino-propyl)-1,7,8,9-tetrahydro-pyrano[2,3-g]indazole-8,9-diol Step A: Benzyl (S)-2-(6-hydroxy-1H-indazol-1-yl)-1-methylethylcarbamate To a suspension of 1-((S)-2-aminopropyl)-1H-indazol-6-ol (2.00 g, 10.5 mmol) in THF (20 mL) was added saturated aqueous sodium bicarbonate (10 mL) and benzyl chloroformate (1.50 mL, 1.5 mmol). The mixture was stirred until all of the solid starting amine dissolved. After stirring at ambient temperature for 45 minutes saturated aqueous sodium bicarbonate (150 mL) was added and the mixture was extracted with ethyl acetate (3×150 mL). The combined extracts were dried ($MgSO_4$) and evaporated to give a tan foam (2.65 g, 78%): LC/MS (+APCI) m/z 326 (M+H).

Step B: Benzyl (S)-1-Methyl-2-(6-prop-2-ynyloxy-indazol-1-yl)-ethylcarbamate

A solution of the product from Step A (2.88 g, 8.86 mmol) in acetone (100 mL) was degassed with reduced pressure and nitrogen. Powdered potassium carbonate (1.35 g, 9.75 mmol) and propargyl bromide (80% by weight in toluene, 0.99 mL, 8.86 mmol) were added the mixture was refluxed for 24 hours. The cooled reaction mixture was filtered and the filtrate was evaporated to a yellow oil (3.15 g) which was purified by chromatography (silica, 20% to 50% ethyl acetate in hexane) to give a white solid (2.37 g, 74%): mp 104–106° C.; LC/MS (+APCI) m/z 364 (M+H).

Step C: Benzyl (S)-1-Methyl-2-(7H-pyrano[2,3-g]indazol-1-yl)-ethylcarbamate

The product from Step B (2.37 g, 6.53 mmol) was heated in mesitylene (40 mL) in a manner similar to that described in Example 4, Step B to give, following purification (silica, 20% to 50% ethyl acetate in hexane), an oil (1.01 g, 43%): LC/MS (+APCI) m/z 364 (M+H).

Step D: Benzyl (S)-2-((8R*,9S*)-8,9-Dihydroxy-8,9-dihydro-7H-pyrano[2,3-g]indazol-1-yl)-1-methyl-ethylcarbamate A solution of the product of Step C (1.01 g, 2.78 mmol) in a mixture of tert-butyl alcohol (20 mL) and water (20 mL) was added to a mixture of tert-butyl alcohol (25 mL), water (25 mL), AD-mix-α (4.2 g) and methanesulfonoamide (0.26 g, 2.8 mmol) at room temperature. The reaction mixture was stirred for 24 hours followed by the addition of powdered sodium sulfite (5 g) and stirred for an additional hour. Saturated aqueous sodium bicarbonate (150 mL) was added to the mixture, which was extracted with ethyl acetate (3×150 mL). The combined extracts were dried (MgSO$_4$) and evaporated to an oil (1.03 g) which was purified by chromatography (silica, 50% ethyl acetate in hexane to ethyl acetate) to give two products. Product A was obtained as a white foam (0.16 g, 15%): diastereomeric ratio 4:1; LC/MS (+APCI) m/z 398 (M+H). Product B was a colorless amorphous solid (0.18 g, 16%): mp 64–67° C.; diastereomeric ratio 1:4; LC/MS (+APCI) m/z 398 (M+H).

Step E: (8R*,9S*)-1-[(2S)-2-aminopropyl]-1,7,8,9-tetrahydropyrano[2,3-g]indazole-8,9-diol A solution of product A from Step D (0.14 g, 0.354 mmol) in THF (20 mL) was treated as described in Example 2, Step J to give the free base as a colorless solid (50 mg, 54%): mp 115–117° C.; [α]$_D$ –79.3° (c 0.27, THF), diastereomeric ratio 4:1; LC/MS (+APCI) m/z 264 (M+H) and 246 (M+H–H$_2$O).

EXAMPLE 8

(S)-2-(8,9-Dihydro-7H-pyrano[2,3-g]indazol-1-yl)-1-methyl-ethylamine dihydrochloride Step A: (R)-1-(7H-Pyrano[2,3-g]indazol-1-yl)-propan-2-ol A mixture of the product from Example 4, Step B (0.26 g, 0.76 mmol) and tetrabutylammonium fluoride (1 M, 1.52 mmol) in THF (3 mL) was stirred at ambient temperature for 4 h. The reaction mixture was added to a saturated aqueous solution of sodium bicarbonate (10 mL) and this mixture was extracted with ethyl acetate (3×5 mL). The combined extracts were dried and evaporated to a residue which was purified by chromatography (silica, 10% to 40% ethyl acetate in hexane) to give the alcohol as an oil (0.14 g, 81%): LC/MS (+APCI) m/z 231 (M+H).

Step B: 1-((S)-2-Azido-propyl)-1,7-dihydro-pyrano[2,3-g]indazole

To a solution of the product from Step A (0.14 g, 0.61 mmol) and triethylamine (0.18 g, 1.8 mmol) in anhydrous THF (50 ml) at 0° C. was added methanesulfonic anhydride (0.16 g, 0.92 mmol). The mixture was stirred for 10 min and sodium azide (0.40 g, 6.1 mmol) was added; the solvent was evaporated and anhydrous DMF (50 mL) added followed by heating at 110° C. for 3 h. The mixture was cooled, poured into a saturated solution of sodium bicarbonate (80 mL) and extracted with ethyl acetate (3×60 mL). The combined extracts were dried, filtered, and evaporated to a residue which was purified by chromatography (silica, 10% ethyl acetate in hexane) to give an oil (0.06 g, 39%): LC/MS (+APCI) m/z 256 (M+H).

Step C: (S)-2-(8,9-Dihydro-7H-pyrano[2,3-g]indazol-1-yl)-1-methyl-ethylamine dihydrochloride A solution of the product from Step B in methanol was treated as described in Example 2, Step J to give a yellowish solid (0.07 g, 77%): mp>120° C.; LC/MS (+APCI) m/z 232 (M+H). The free base form was obtained as a colorless solid: mp 95–98° C.; [α]$_D$ –66.7° (c 0.445, THF). Analysis. Calculated for C$_{13}$H$_{17}$N$_3$O: C, 67.51; H, 7.41; N, 18.17. Found: C, 67.47; H, 7.51; N, 17.91.

EXAMPLE 9

(S)-1-Methyl-2-(7H-pyrano[2,3-g]indazol-1-yl)-ethylamine

To a solution of the product from Example 8, Step B (0.10 g, 0.39 mmol) in dry THF (20 ml) at 0° C. was added a solution of lithium aluminum hydride (0.39 mL, 1.56 mmol of a 1 M solution in THF) and the mixture was allowed to warm to room temperature (1 h) with stirring. Aqueous potassium hydroxide (2 M, 0.02 mL) was added to the reaction mixture and the solids that formed were removed by filtration. The filtrate was evaporated to a yellow oil (0.05 g, 56%): LC/MS (+APCI) m/z 230. Analysis. Calculated for C$_{13}$H$_{15}$N$_3$O.0.17H$_2$O: C, 67.26; H, 6.60; N, 18.10. Found: C, 67.35; H, 6.45; N, 17.76.

EXAMPLE 10

1-((S)-2-Amino-propyl)-1H-pyrano[2,3-g]indazol-7-one trifluoroacetate

A suspension of 1-((S)-2-amino-propyl)-1H-indazol-6-ol (1.00 g, 5.23 mmol) and malic acid (0.74 g, 5.5 mmol) in concentrated sulfuric acid (3 mL) was heated at 80° C. for 48 hr and at 90° C. for 24 hr. The reaction mixture was neutralized with sodium phosphate (dibasic, to pH 7) and brine (100 mL) was added followed by extraction of this mixture with THF (3×100 mL). The combined extracts were dried (MgSO$_4$) and evaporated to give a yellow residue (0.54 g) which was purified using reversed phase chromatography (C-18, water/acetonitrile, 0.1% trifluoroacetic acid) to give a yellow oil (70 mg): LC/MS (+APCI) m/z 244 (M+H).

EXAMPLE 11

9-Amino-1-((S)-2-amino-propyl)-1,7,8,9-tetrahydro-pyrano[2,3-g]indazol-8-ol

Step A: Benzyl (S)-2-(8-Bromo-9-hydroxy-8,9-dihydro-7H-pyrano[2,3-g]indazol-1-yl)-1-methylethylcarbamate To a solution of the product from Example 7, Step C (1.35 g, 3.71 mmol) in a mixture of dimethylsulfoxide and water (20 mL:2 mL) at 0° C. was added N-bromosuccinimide (0.69 g, 3.89 mmol). This mixture was stirred for 2 h, combined with water (100 mL), and extracted with ethyl acetate (3×100 mL). The combined extracts were dried and concentrated to a residue which was purified by chromatography (silica, 20% ethyl acetate in hexane) to give an oil (1.18 g, 69%): LC/MS m/z 460, 462 (M+H).

Step B: Benzyl (S)-2-(9-Azido-8-Bromo-8,9-dihydro-7H-pyrano[2,3-g]indazol-1-yl)-1-methylethylcarbamate A mixture of the product from Step A (0.31 g, 0.67 mmol) and sodium azide (0.65 g, 10 mmol) in dimethylsulfoxide (20 mL) was heated at 80° C. for 3 h, cooled to room temperature, and extracted with ethyl acetate. The combined extracts were dried and concentrated to a residue which was purified by chromatography (silica, 30% ethyl acetate in hexane) to give an oil (0.26 g, 68%): LC/MS (+APCI) m/z 423 (M+H).

Step C: 9-Amino-1-((S)-2-amino-propyl)-1,7,8,9-tetrahydro-pyrano[2,3-g]indazol-8-ol The product from step B (0.26 g, 0.30 mmol) and Pd/C (10%, 0.026 g) were mixed with methanol (5 mL) and placed under a hydrogen atmosphere for 18 h. The mixture was filtered and evaporated to give a yellowish solid (0.155 g, 96%): mp 84–88° C.; LC/MS (+APCI) m/z 263 (M+H).

EXAMPLE 12

1-((S)-2-Amino-propyl)-9-methoxy-1,7,8,9-tetrahydro-pyrano[2,3-g]indazol-8-ol

Step A: Benzyl (S)-2-(8-hydroxy-9-methoxy-8,9-dihydro-7H-pyrano[2,3-g]indazol-1-yl)-1-methylethylcarbamate To a solution of the product from Example 11, Step A (0.46 g, 1.12 mmol) in tetrahydrofuran (50 mL) was added 2 N sodium hydroxide (6 mL). After stirring for 10 min, methanol (10 mL) was added and the mixture stirred for 1 h followed by evaporation to a residue, which was mixed with water (50 mL) and extracted with ethyl acetate (3×50 mL). The combined extracts were dried over magnesium sulfate, filtered and evaporated to a residue, which was purified by chromatography (silica, 20 to 35% ethyl acetate in hexane) to give an oil (0.45 g): LC/MS (+APCI) m/z 378 (M+H).

Step B: 1-((S)-2-Amino-propyl)-9-methoxy-1,7,8,9-tetrahydro-pyrano[2,3-g]indazol-8-ol To a solution of the product from Step A (0.22 g, 0.58 mmol) in methanol (5 mL) was added trifluoroacetic acid (5 mL) and the mixture was stirred at ambient temperature for 2 days. The mixture was evaporated to a residue, which was stirred with a 2 N solution of hydrogen chloride in ethanol (5 mL) and evaporated to afford a solid (0.21 g): mp 105–108° C.; LC/MS (+APCI) m/z 278 (M+H).

The following topical ophthalmic formulations are useful according to the present invention administered 1–4 times per day according to the discretion of a skilled clinician.

EXAMPLE 13

| Ingredients | Amount (wt %) |
| --- | --- |
| Compound of Example 3 | 0.01–2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 14

| Ingredients | Amount (wt %) |
| --- | --- |
| Compound of Example 3 | 0.01–2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 15

| Ingredients | Amount (wt %) |
| --- | --- |
| Compound of Example 3 | 0.01–2% |
| Guar gum | 0.4–6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 16

| Ingredients | Amount (wt %) |
| --- | --- |
| Compound of Example 3 | 0.01–2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A compound represented by Formula I:

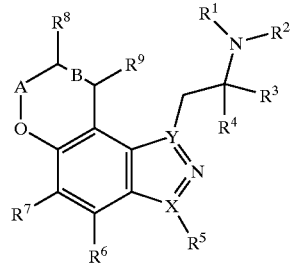

wherein $R^1$ and $R^2$ are independently chosen from hydrogen or an alkyl group;

$R^3$ and $R^4$ are independently hydrogen or an alkyl group or;

$R^3$ and $R^4$ and the carbon atom to which they are attached form a cycloalkyl ring, or;

$R^2$ and $R^3$ together form a saturated $(CH_2)_m$ heterocycle;

$R^5$ is hydrogen, halogen, or a substituted or unsubstituted alkyl group;

$R^6$ and $R^7$ are independently hydrogen, halogen, cyano, an alkylthio, or a substituted or unsubstituted alkyl group;

$R^8$ and $R^9$ are independently hydrogen, hydroxyl, a substituted or unsubstituted alkyl group, an alkoxy, =O, $NR^{10}R^{11}$, $OC(=O)NR^1R^2$, $OC(=O)C_{1-4}$alkyl, or an alkylthiol;

$R^{10}$ and $R^{11}$ are independently hydrogen, a substituted or unsubstituted alkyl group, $C(=O)C_{1-4}$ alkyl, $C(=O)OC_{1-4}$ alkyl, or $C(=O)NR^1R^2$ or $R^{10}$ and $R^{11}$ together complete a saturated 5 or 6-membered heterocyclic ring, or $R^{10}$ and $R^{11}$ together complete a saturated 6-membered heterocyclic ring that includes an additional heteroatom selected from N, O, or S;

A is $(CH_2)_n$, C=O, or $CHC_{1-4}$alkyl;

B is either a single or a double bond, wherein when B is a double bond, $R^8$ and $R^9$ are selected from hydrogen, or a substituted or unsubstituted alkyl group;

m=2–4;

n=0–2;

X and Y are either N or C, wherein X and Y are different; and the dashed bonds denote a suitably appointed single and double bond, and wherein when X=C and A=(CH$_2$)$_n$ where n=0, then at least one of R$^8$ or R$^9$ is a substituted alkyl, OC(=O)NR$^1$R$^2$, OC(=O)C$_{1-4}$alkyl, an alkylthiol, or NR$^{10}$R$^{11}$ wherein at least one of R$^{10}$ or R$^{11}$ is a substituted alkyl group, C(=O)OC$_{1-4}$ alkyl, or C(=O)NR$^1$R$^2$ or wherein R$^{10}$ and R$^{11}$ together complete a saturated 5 or 6-membered heterocyclic ring, or wherein R$^{10}$ and R$^{11}$ together complete a saturated 6-membered heterocyclic ring that includes an additional heteroatom selected from N, O, or S.

2. The compound of claim 1, wherein R$^2$ and R$^3$ form a saturated (CH$_2$)$_m$ heterocycle.

3. The compound of claim 1, wherein said R$^3$ and R$^4$ together form a cyclopropyl ring.

4. The compound of claim 1, wherein R$^1$ and R$^2$ are independently chosen from hydrogen or C$_{1-4}$alkyl;

R$^3$ and R$^4$ are independently chosen from hydrogen or C$_{1-4}$alkyl, or R$^2$ and R$^3$ together form a saturated (CH$_2$)$_m$ heterocycle;

R$^5$ is chosen from hydrogen, halogen, or C$_{1-6}$alkyl;

R$^6$ and R$^7$ are independently chosen from hydrogen, halogen, cyano, C$_{1-4}$alkylthio, C$_{1-4}$alkyl, or C$_{1-4}$alkyl substituted by halogen;

R$^8$ and R$^9$ are chosen from hydrogen, hydroxyl, C$_{1-6}$alkyl, C$_{1-6}$alkoxy, NR$^{10}$R$^{11}$, or C$_{1-6}$alkyl substituted with halogen, hydroxyl, or NR$^{10}$R$^{11}$;

R$^{10}$ and R$^{11}$ are independently chosen from hydrogen or C$_{1-4}$alkyl or C(=O)C$_{1-4}$alkyl or R$^{10}$ and R$^{11}$ together complete a saturated 5 or 6-membered heterocyclic ring, or R$^{10}$ and R$^{11}$ together complete a saturated 6-membered heterocyclic ring that includes an additional heteroatom selected from N, O, or S;

A is (CH$_2$)$_n$ or CHC$_{1-4}$alkyl;

B is either a single or double bond, wherein when B is a double bond, R$^8$ and R$^9$ are selected from hydrogen, C$_{1-4}$alkyl, or C$_{1-4}$alkyl substituted by halogen, hydroxy, or NR$^{10}$R$^{11}$;

m=3–4;

n=1–2; and

X and Y are either N or C, wherein X and Y cannot be the same; and the dashed bonds denote a suitably appointed single and double bond.

5. The compound of claim 1, wherein R$^1$ and R$^2$ are independently chosen from hydrogen or C$_{1-4}$alkyl;

R$^3$ is C$_{1-2}$alkyl, or R$^2$ and R$^3$ together are (CH$_2$)$_3$ to form pyrrolidine;

R$^4$ is hydrogen;

R$^5$ chosen from hydrogen or C$_{1-6}$alkyl;

R$^6$ and R$^7$ are independently chosen from hydrogen, halogen, or C$_{1-4}$alkyl;

R$^8$ and R$^9$ are independently chosen from hydrogen, hydroxyl, C$_{1-6}$alkoxy, NR$^{10}$R$^{11}$, or C$_{1-6}$alkyl substituted with hydroxyl or NR$^{10}$R$^{11}$;

R$^{10}$ and R$^{11}$ are independently chosen from hydrogen, C$_{1-4}$alkyl or C(=O)C$_{1-4}$alkyl or R$^{10}$ and R$^{11}$ together complete a saturated 5 or 6-membered heterocyclic ring, or R$^{10}$ and R$^{11}$ together complete a saturated 6-membered heterocyclic ring that includes an additional heteroatom selected from N, O, or S;

A is (CH$_2$)$_n$;

B is a single bond;

n=1;

X is C and Y is N; and the dashed bonds denote a suitably appointed single and double bond.

6. The compound of claim 1, wherein said compound is:

1-(2-Aminopropyl)-1,7,8,9-tetrahydro-pyrano[2,3-g]indazol-8-ol;

1-((S)-2-Aminopropyl)-1,7,8,9-tetrahydro-pyrano[2,3-g]indazol-8-ol;

(R)-1-((S)-2-Aminopropyl)-1,7,8,9-tetrahydro-pyrano[2,3-g]indazol-8-ol;

(S)-1-((S)-2-Aminopropyl)-1,7,8,9-tetrahydro-pyrano[2,3-g]indazol-8-ol;

1-((S)-2-Aminopropyl)-3-methyl-1,7,8,9-tetrahydro-pyrano[2,3-g]indazol-8-ol;

1-(S)-1-Pyrrolidin-2-ylmethyl-1,7,8,9-tetrahydro-pyrano[2,3-g]indazol-8-ol;

1-((S)-2-Aminopropyl)-5-fluoro-1,7,8,9-tetrahydro-pyrano[2,3-g]indazol-8-ol;

(R)-1-((S)-2-Aminopropyl)-1,7,8,9-tetrahydro-pyrano[2,3-g]indazol-8-ylamine;

[1-((S)-2-Aminopropyl)-1,7,8,9-tetrahydro-pyrano[2,3-g]indazol-8-yl]-dimethylamine;

[1-((S)-2-Aminopropyl)-1,7,8,9-tetrahydro-pyrano[2,3-g]indazol-8-yl]-methanol;

1-((S)-2-Aminopropyl)-1,7,8,9-tetrahydro-pyrano[2,3-g]indazole-8,9-diol;

1-((S)-2-Aminopropyl)-9-methoxy-1,7,8,9-tetrahydro-pyrano[2,3-g]indazol-8-ol;

1-(2-Aminopropyl)-3,7,8,9-tetrahydro-pyrano[3,2-e]indazol-8-ol;

1-(Pyrrolidin-2-ylmethyl)-3,7,8,9-tetrahydro-pyrano[3,2-e]indazol-8-ol;

1-((S)-2-Aminopropyl)-3,7,8,9-tetrahydro-pyrano[3,2-e]indazol-8-ol;

1-((S)-2-Aminopropyl)-3-methyl-3,7,8,9-tetrahydro-pyrano[3,2-e]indazol-8-ol; or combinations thereof.

7. The compound of claim 1, wherein said X is N.

8. The compound of claim 1, wherein said X is C.

9. A method of controlling normal or elevated intraocular pressure comprising administering a pharmaceutically effective amount of a composition comprising at least one compound represented by the following formula:

wherein R$^1$ and R$^2$ are independently chosen from hydrogen or an alkyl group;

R$^3$ and R$^4$ are independently hydrogen or an alkyl group or;

R$^3$ and R$^4$ and the carbon atom to which they are attached form a cycloalkyl ring, or;

R$^2$ and R$^3$ together form a saturated (CH$_2$)$_m$ heterocycle;

R$^5$ is hydrogen, halogen, or a substituted or unsubstituted alkyl group;

R$^6$ and R$^7$ are independently hydrogen, halogen, cyano, an alkylthio, or a substituted or unsubstituted alkyl group;

R$^8$ and R$^9$ are independently hydrogen, hydroxyl, a substituted or unsubstituted alkyl group, an alkoxy, =O, NR$^{10}$R$^{11}$, OC(=O)NR$^1$R$^2$, OC(=O)C$_{1-4}$alkyl, or an alkylthiol;

R$^{10}$ and R$^{11}$ are independently hydrogen, a substituted or unsubstituted alkyl group, C(=O)C$_{1-4}$ alkyl, C(=O)C$_{1-4}$ alkyl, or C(=O)NR$^1$R$^2$ or R$^{10}$ and R$^{11}$ together complete a saturated 5 or 6-membered heterocyclic ring or R$^{10}$ and R$^{11}$ together complete a saturated 6-membered heterocyclic ring that includes an additional heteroatom selected from N, O, or S;

A is (CH$_2$)$_n$, C=O, or CHC$_{1-4}$alkyl;

B is either a single or a double bond, wherein when B is a double bond, R$^8$ and R$^9$ are selected from hydrogen, or a substituted or unsubstituted alkyl group;

m=2–4;

n=0–2;

X and Y are either N or C, wherein X and Y are different; and the dashed bonds denote a suitably appointed single and double bond.

10. The method of claim 9, wherein R$^2$ and R$^3$ form a saturated (CH$_2$)$_m$ heterocycle.

11. The method of claim 9, wherein said R$^3$ and R$^4$ together form a cyclopropyl ring.

12. The method of claim 9, wherein R$^1$ and R$^2$ are independently chosen from hydrogen or C$_{1-4}$alkyl;

R$^3$ and R$^4$ are independently chosen from hydrogen or C$_{1-4}$alkyl, or R$^2$ and R$^3$ together form a saturated (CH$_2$)$_m$ heterocycle;

R$^5$ is chosen from hydrogen, halogen, or C$_{1-6}$alkyl;

R$^6$ and R$^7$ are independently chosen from hydrogen, halogen, cyano, C$_{1-4}$alkylthio, C$_{1-4}$alkyl, or C$_{1-4}$alkyl substituted by halogen;

R$^8$ and R$^9$ are chosen from hydrogen, hydroxyl, C$_{1-6}$alkyl, C$_{1-6}$alkoxy, NR$^{10}$R$^{11}$, or C$_{1-6}$alkyl substituted with halogen, hydroxyl, or NR$^{10}$R$^{11}$;

R$^{10}$ and R$^{11}$ are independently chosen from hydrogen or C$_{1-4}$alkyl or C(=O)C$_{1-4}$alkyl or R$^{10}$ and R$^{11}$ together complete a saturated 5 or 6-membered heterocyclic ring, or R$^{10}$ and R$^{11}$ together complete a saturated 6-membered heterocyclic ring that includes an additional heteroatom selected from N, O, or S;

A is (CH$_2$)$_n$ or CHC$_{1-4}$alkyl;

B is either a single or double bond, wherein when B is a double bond, R$^8$ and R$^9$ are selected from hydrogen, C$_{1-4}$alkyl, or C$_{1-4}$alkyl substituted by halogen, hydroxy, or NR$^{10}$R$^{11}$;

m=3–4;

n=1–2; and

X and Y are either N or C, wherein X and Y cannot be the same; and the dashed bonds denote a suitably appointed single and double bond.

13. The method of claim 9, wherein R$^1$ and R$^2$ are independently chosen from hydrogen or C$_{1-4}$alkyl;

R$^3$ is C$_{1-2}$alkyl, or R$^2$ and R$^3$ together are (CH$_2$)$_3$ to form pyrrolidine;

R$^4$ is hydrogen;

R$^5$ is chosen from hydrogen or C$_{1-6}$alkyl;

R$^6$ and R$^7$ are independently chosen from hydrogen, halogen, or C$_{1-4}$alkyl;

R$^8$ and R$^9$ are independently chosen from hydrogen, hydroxyl, C$_{1-6}$alkoxy, NR$^{10}$R$^{11}$, or C$_{1-6}$alkyl substituted with hydroxyl or NR$^{10}$R$^{11}$;

R$^{10}$ and R$^{11}$ are independently chosen from hydrogen, C$_{1-4}$alkyl or C(=O)C$_{1-4}$alkyl or R$^{10}$ and R$^{11}$ together complete a saturated 5 or 6-membered heterocyclic ring, or R$^{10}$ and R$^{11}$ together complete a saturated 6-membered heterocyclic ring that includes an additional heteroatom selected from N, O, or S;

A is (CH$_2$)$_n$;

B is a single bond;

n=1;

X is C and Y is N; and the dashed bonds denote a suitably appointed single and double bond.

14. The method of claim 9, wherein said compound is:

1-(2-Aminopropyl)-1,7,8,9-tetrahydro-pyrano[2,3-g]indazol-8-ol;

1-((S)-2-Aminopropyl)-1,7,8,9-tetrahydro-pyrano[2,3-g]indazol-8-ol;

(R)-1-((S)-2-Aminopropyl)-1,7,8,9-tetrahydro-pyrano[2,3-g]indazol-8-ol;

(S)-1-((S)-2-Aminopropyl)-1,7,8,9-tetrahydro-pyrano[2,3-g]indazol-8-ol;

1-((S)-2-Aminopropyl)-3-methyl-1,7,8,9-tetrahydro-pyrano[2,3-g]indazol-8-ol;

1-(S)-1-Pyrrolidin-2-ylmethyl-1,7,8,9-tetrahydro-pyrano[2,3-g]indazol-8-ol;

1-((S)-2-Aminopropyl)-5-fluoro-1,7,8,9-tetrahydro-pyrano[2,3-g]indazol-8-ol;

(R)-1-((S)-2-Aminopropyl)-1,7,8,9-tetrahydro-pyrano[2,3-g]indazol-8-ylamine;

[1-((S)-2-Aminopropyl)-1,7,8,9-tetrahydro-pyrano[2,3-g]indazol-8-yl]-dimethylamine;

[1-((S)-2-Aminopropyl)-1,7,8,9-tetrahydro-pyrano[2,3-g]indazol-8-yl]-methanol;

1-((S)-2-Aminopropyl)-1,7,8,9-tetrahydro-pyrano[2,3-g]indazole-8,9-diol;

1-((S)-2-Aminopropyl)-9-methoxy-1,7,8,9-tetrahydro-pyrano[2,3-g]indazol-8-ol;

1-(2-Aminopropyl)-3,7,8,9-tetrahydro-pyrano[3,2-e]indazol-8-ol;

1-(Pyrrolidin-2-ylmethyl)-3,7,8,9-tetrahydro-pyrano[3,2-e]indazol-8-ol;

1-((S)-2-Aminopropyl)-3,7,8,9-tetrahydro-pyrano[3,2-e]indazol-8-ol;

1-((S)-2-Aminopropyl)-3-methyl-3,7,8,9-tetrahydro-pyrano[3,2-e]indazol-8-ol; or combinations thereof.

15. The method of claim 9, wherein said X is N.

16. The method of claim 9, wherein said X is C.

17. A method for the treatment of glaucoma comprising administering a pharmaceutically effective amount of a composition comprising at least one compound represented by the following formula:

wherein R$^1$ and R$^2$ are independently chosen from hydrogen or an alkyl group;

R$^3$ and R$^4$ are independently hydrogen or an alkyl group or;

R$^3$ and R$^4$ and the carbon atom to which they are attached form a cycloalkyl ring, or;

R$^2$ and R$^3$ together form a saturated (CH$_2$)$_m$ heterocycle;

R$^5$ is hydrogen, halogen, or a substituted or unsubstituted alkyl group;

R$^6$ and R$^7$ are independently hydrogen, halogen, cyano, an alkylthio, or a substituted or unsubstituted alkyl group;

R$^8$ and R$^9$ are independently hydrogen, hydroxyl, a substituted or unsubstituted alkyl group, an alkoxy, =O, NR$^{10}$R$^{11}$, OC(=O)NR$^1$R$^2$, OC(=O)C$_{1-4}$alkyl, or an alkylthiol;

R$^{10}$ and R$^{11}$ are independently hydrogen, a substituted or unsubstituted alkyl group, C(=O)C$_{1-4}$ alkyl, C(=O)OC$_{1-4}$ alkyl, or C(=O)NR$^1$R$^2$ or R$^{10}$ and R$^{11}$ together complete a saturated 5 or 6-membered heterocyclic ring or R$^{10}$ and R$^{11}$ together complete a saturated 6-membered heterocyclic ring that includes an additional heteroatom selected from N, O, or S;

A is (CH$_2$)$_n$, C=O, or CHC$_{1-4}$alkyl;

B is either a single or a double bond, wherein when B is a double bond, R$^8$ and R$^9$ are selected from hydrogen, or a substituted or unsubstituted alkyl group;

m=2–4;

n=0–2;

X and Y are either N or C, wherein X and Y are different; and the dashed bonds denote a suitably appointed single and double bond.

18. The method of claim 17, wherein R$^1$ and R$^2$ are independently chosen from hydrogen or C$_{1-4}$alkyl;

R$^3$ and R$^4$ are independently chosen from hydrogen or C$_{1-4}$alkyl, or R$^2$ and R$^3$ together form a saturated (CH$_2$)$_m$ heterocycle;

R$^5$ is chosen from hydrogen, halogen, or C$_{1-6}$alkyl;

R$^6$ and R$^7$ are independently chosen from hydrogen, halogen, cyano, C$_{1-4}$alkylthio, C$_{1-4}$alkyl, or C$_{1-4}$alkyl substituted by halogen;

R$^8$ and R$^9$ are chosen from hydrogen, hydroxyl, C$_{1-6}$alkyl, C$_{1-6}$alkoxy, NR$^{10}$R$^{11}$, or C$_{1-6}$alkyl substituted with halogen, hydroxyl, or NR$^{10}$R$^{11}$;

R$^{10}$ and R$^{11}$ are independently chosen from hydrogen or C$_{1-4}$alkyl or C(=O)C$_{1-4}$alkyl or R$^{10}$ and R$^{11}$ together can complete a saturated 5 or 6-membered heterocyclic ring, or R$^{10}$ and R$^{11}$ together complete a saturated 6-membered heterocyclic ring that includes an additional heteroatom selected from N, O, or S;

A is (CH$_2$)$_n$ or CHC$_{1-4}$alkyl;

B is either a single or double bond, wherein when B is a double bond, R$^8$ and R$^9$ are selected from hydrogen, C$_{1-4}$alkyl, or C$_{1-4}$alkyl substituted by halogen, hydroxy, or NR$^{10}$R$^{11}$;

m=3–4;

n=1–2; and

X and Y are either N or C, wherein X and Y cannot be the same; and the dashed bonds denote a suitably appointed single and double bond.

19. The method of claim 17, wherein R$^1$ and R$^2$ are independently chosen from hydrogen or C$_{1-4}$alkyl;

R$^3$ is C$_{1-2}$alkyl, or R$^2$ and R$^3$ together are (CH$_2$)$_3$ to form pyrrolidine;

R$^4$ is hydrogen;

R$^5$ is chosen from hydrogen or C$_{1-6}$alkyl;

R$^6$ and R$^7$ are independently chosen from hydrogen, halogen, or C$_{1-4}$alkyl;

R$^8$ and R$^9$ are independently chosen from hydrogen, hydroxyl, C$_{1-6}$alkoxy, NR$^{10}$R$^{11}$, or C$_{1-6}$alkyl substituted with hydroxyl or NR$^{10}$R$^{11}$;

R$^{10}$ and R$^{11}$ are independently chosen from hydrogen, C$_{1-4}$alkyl or C(=O)C$_{1-4}$alkyl or R$^{10}$ and R$^{11}$ together complete a saturated 5 or 6-membered heterocyclic ring, or R$^{10}$ and R$^{11}$ together complete a saturated 6-membered heterocyclic ring that includes an additional heteroatom selected from N, O, or S;

A is (CH$_2$)$_n$;

B is a single bond;

n=1;

X is C and Y is N; and the dashed bonds denote a suitably appointed single and double bond.

20. The method of claim 17, wherein said compound is:

1-(2-Aminopropyl)-1,7,8,9-tetrahydro-pyrano[2,3-g]indazol-8-ol;

1-((S)-2-Aminopropyl)-1,7,8,9-tetrahydro-pyrano[2,3-g]indazol-8-ol;

(R)-1-((S)-2-Aminopropyl)-1,7,8,9-tetrahydro-pyrano[2,3-g]indazol-8-ol;

(S)-1-((S)-2-Aminopropyl)-1,7,8,9-tetrahydro-pyrano[2,3-g]indazol-8-ol;

1-((S)-2-Aminopropyl)-3-methyl-1,7,8,9-tetrahydro-pyrano[2,3-g]indazol-8-ol;

1-(S)-1-Pyrrolidin-2-ylmethyl-1,7,8,9-tetrahydro-pyrano[2,3-g]indazol-8-ol;

1-((S)-2-Aminopropyl)-5-fluoro-1,7,8,9-tetrahydro-pyrano[2,3-g]indazol-8-ol;

(R)-1-((S)-2-Aminopropyl)-1,7,8,9-tetrahydro-pyrano[2,3-g]indazol-8-ylamine;

[1-((S)-2-Aminopropyl)-1,7,8,9-tetrahydro-pyrano[2,3-g]indazol-8-yl]-dimethylamine;

[1-((S)-2-Aminopropyl)-1,7,8,9-tetrahydro-pyrano[2,3-g]indazol-8-yl]-methanol;

1-((S)-2-Aminopropyl)-1,7,8,9-tetrahydro-pyrano[2,3-g]indazole-8,9-diol;

1-((S)-2-Aminopropyl)-9-methoxy-1,7,8,9-tetrahydro-pyrano[2,3-g]indazol-8-ol;

1-(2-Aminopropyl)-3,7,8,9-tetrahydro-pyrano[3,2-e]indazol-8-ol;

1-(Pyrrolidin-2-ylmethyl)-3,7,8,9-tetrahydro-pyrano[3,2-e]indazol-8-ol;

1-((S)-2-Aminopropyl)-3,7,8,9-tetrahydro-pyrano[3,2-e]indazol-8-ol;

1-((S)-2-Aminopropyl)-3-methyl-3,7,8,9-tetrahydro-pyrano[3,2-e]indazol-8-ol; or combinations thereof.

21. A pharmaceutical composition comprising the compound of claim 1 and at least one carrier.

22. A method to activate or bind to serotonin receptors to treat glaucoma or to control normal or elevated intraocular pressure comprising administering an effective amount of at least one compound of claim 1 to a patient.

23. The compound of claim 1, wherein X=C and A=$(CH_2)_n$, wherein n is 1 or 2.

24. The compound of claim 1, wherein X=C and A=$(CH_2)_n$ and n=0 and $R^8$ or $R^9$ is a substituted alkyl group.

25. The compound of claim 1, wherein X=C, A=$(CH_2)_n$ and n=0 and B is a single bond.

* * * * *